(12) United States Patent
Kim et al.

(10) Patent No.: US 11,504,090 B2
(45) Date of Patent: Nov. 22, 2022

(54) ULTRASOUND DIAGNOSIS APPARATUS AND METHOD OF OPERATING THE SAME

(71) Applicant: SAMSUNG MEDISON CO., LTD., Hongcheon-gun (KR)

(72) Inventors: Kang-sik Kim, Seongnam-si (KR); Bae-hyeong Kim, Yongin-si (KR); Jong-keun Song, Yongin-si (KR)

(73) Assignee: SAMSUNG MEDISON CO. LTD., Hongcheon-gun (KR)

( * ) Notice: Subject to any disclaimer, the term of this patent is extended or adjusted under 35 U.S.C. 154(b) by 875 days.

(21) Appl. No.: 15/206,773

(22) Filed: Jul. 11, 2016

(65) Prior Publication Data

US 2017/0128046 A1 May 11, 2017

(30) Foreign Application Priority Data

Nov. 11, 2015 (KR) .................. 10-2015-0158111

(51) Int. Cl.
*A61B 8/08* (2006.01)
*A61B 8/14* (2006.01)
(Continued)

(52) U.S. Cl.
CPC .............. *A61B 8/4483* (2013.01); *A61B 8/06* (2013.01); *A61B 8/14* (2013.01); *A61B 8/4405* (2013.01);
(Continued)

(58) Field of Classification Search
None
See application file for complete search history.

(56) References Cited

U.S. PATENT DOCUMENTS 5,494,040 A 2/1996 Nakao et al.
5,808,967 A * 9/1998 Yu .................... B06B 1/0629
367/91
(Continued)

FOREIGN PATENT DOCUMENTS

CN 102164545 A 8/2011
CN 102579078 A 7/2012
(Continued)

OTHER PUBLICATIONS

O'Donnell, "Efficient Parallel Receive Beam Forming for Phased Array Imaging Using Phase Rotation" IEEE Symposium on Ultrasonics, Dec. 1990, pp. 1495-1498 (Year: 1990).*
(Continued)

*Primary Examiner* — Colin T. Sakamoto
(74) *Attorney, Agent, or Firm* — Morgan, Lewis & Bockius LLP

(57) ABSTRACT

An ultrasound diagnosis apparatus includes: a two-dimensional (2D) transducer array in which a plurality of transducers that transmit/receive an ultrasound signal to/from an object are arranged in two dimensions; an analog beamformer configured to perform analog beamforming in a first direction, and perform analog beamforming in a second direction perpendicular to the first direction on signals respectively received by the plurality of transducers; and a digital beamformer configured to perform digital beamforming on the signals that are analog-beamformed in the first direction, and perform digital beamforming on the signals that are analog-beamformed in the second direction.

30 Claims, 17 Drawing Sheets

(51) Int. Cl.
  *A61B 8/06*   (2006.01)
  *G01S 15/89*  (2006.01)
  *G01S 7/52*   (2006.01)
  *A61B 8/00*   (2006.01)
  *G10K 11/34*  (2006.01)

(52) U.S. Cl.
  CPC .......... *A61B 8/4444* (2013.01); *A61B 8/4477* (2013.01); *A61B 8/462* (2013.01); *A61B 8/463* (2013.01); *A61B 8/465* (2013.01); *A61B 8/469* (2013.01); *A61B 8/483* (2013.01); *A61B 8/488* (2013.01); *A61B 8/5207* (2013.01); *G01S 7/52068* (2013.01); *G01S 7/52071* (2013.01); *G01S 7/52073* (2013.01); *G01S 7/52074* (2013.01); *G01S 7/52084* (2013.01); *G01S 7/52095* (2013.01); *G01S 15/8925* (2013.01); *G01S 15/8927* (2013.01); *G01S 15/8993* (2013.01); *G10K 11/34* (2013.01); *G01S 15/8988* (2013.01)

(56) References Cited

U.S. PATENT DOCUMENTS

| | | | |
|---|---|---|---|
| 6,124,828 A | | 9/2000 | Champeau |
| 6,276,211 B1* | | 8/2001 | Smith ................ G01S 7/52095 600/447 |
| 6,436,048 B1* | | 8/2002 | Pesque .................... A61B 8/06 600/447 |
| 6,537,220 B1* | | 3/2003 | Friemel ............... G01S 15/8927 600/447 |
| 6,755,788 B2 | | 6/2004 | Demers et al. |
| 6,761,689 B2 | | 7/2004 | Salgo et al. |
| 8,265,366 B2 | | 9/2012 | Dow et al. |
| 8,880,113 B2 | | 11/2014 | Hardacker et al. |
| 9,427,211 B2 | | 8/2016 | Gerard et al. |
| 10,456,111 B2 | | 10/2019 | Lee et al. |
| 10,485,512 B2 | | 11/2019 | Kim et al. |
| 2002/0045820 A1 | | 4/2002 | Pesque |
| 2003/0023166 A1* | | 1/2003 | Frisa .................. G01S 7/52085 600/443 |
| 2003/0055308 A1* | | 3/2003 | Friemel ................... A61B 8/14 600/15 |
| 2005/0187474 A1 | | 8/2005 | Kwon |
| 2006/0058679 A1* | | 3/2006 | Satoh ...................... A61B 8/12 600/459 |
| 2010/0305449 A1 | | 12/2010 | Wegener et al. |
| 2011/0172536 A1* | | 7/2011 | Do ...................... G01S 7/52074 600/443 |
| 2011/0203374 A1* | | 8/2011 | Oshiki ..................... A61B 8/56 73/602 |
| 2011/0255762 A1* | | 10/2011 | Deischinger ........... A61B 8/463 382/131 |
| 2012/0179043 A1* | | 7/2012 | Kim .................... G01S 7/52017 600/447 |
| 2012/0232397 A1* | | 9/2012 | Ohshima ................ A61B 8/546 600/447 |
| 2012/0330158 A1 | | 12/2012 | Sawayama et al. |
| 2013/0077445 A1 | | 3/2013 | Um et al. |
| 2013/0158409 A1 | | 6/2013 | Kim et al. |
| 2015/0099977 A1 | | 4/2015 | Kim et al. |
| 2017/0007207 A1 | | 1/2017 | Gauthier et al. |

FOREIGN PATENT DOCUMENTS

| | | |
|---|---|---|
| CN | 104510501 A | 4/2015 |
| CN | 104706378 A | 6/2015 |
| EP | 2 474 835 A2 | 7/2012 |
| EP | 2 860 547 A1 | 4/2015 |
| KR | 10-2011-0095906 A | 8/2011 |
| KR | 10-2012-0080093 A | 7/2012 |
| KR | 10-2013-0032163 A | 4/2013 |
| KR | 10-2013-0068529 A | 6/2013 |

OTHER PUBLICATIONS

Bae-Hyung Kim, et al., "Hybrid Beamformation for Volumetric Ultrasound Imaging Scanners Using 2-D Array Transducers", Image Processing (ICIP), 2012, XP032333659, pp. 2297-2300.
Communication dated Apr. 3, 2017, issued by the European Patent Office in counterpart European application No. 16174371.1.
Communication dated Aug. 4, 2020, from the State Intellectual Property Office of People's Republic of China in counterpart Application No. 201610550391.3.
U.S. Notice of Allowance dated Sep. 29, 2022 issued in U.S. Appl. No. 17/883,149.

* cited by examiner

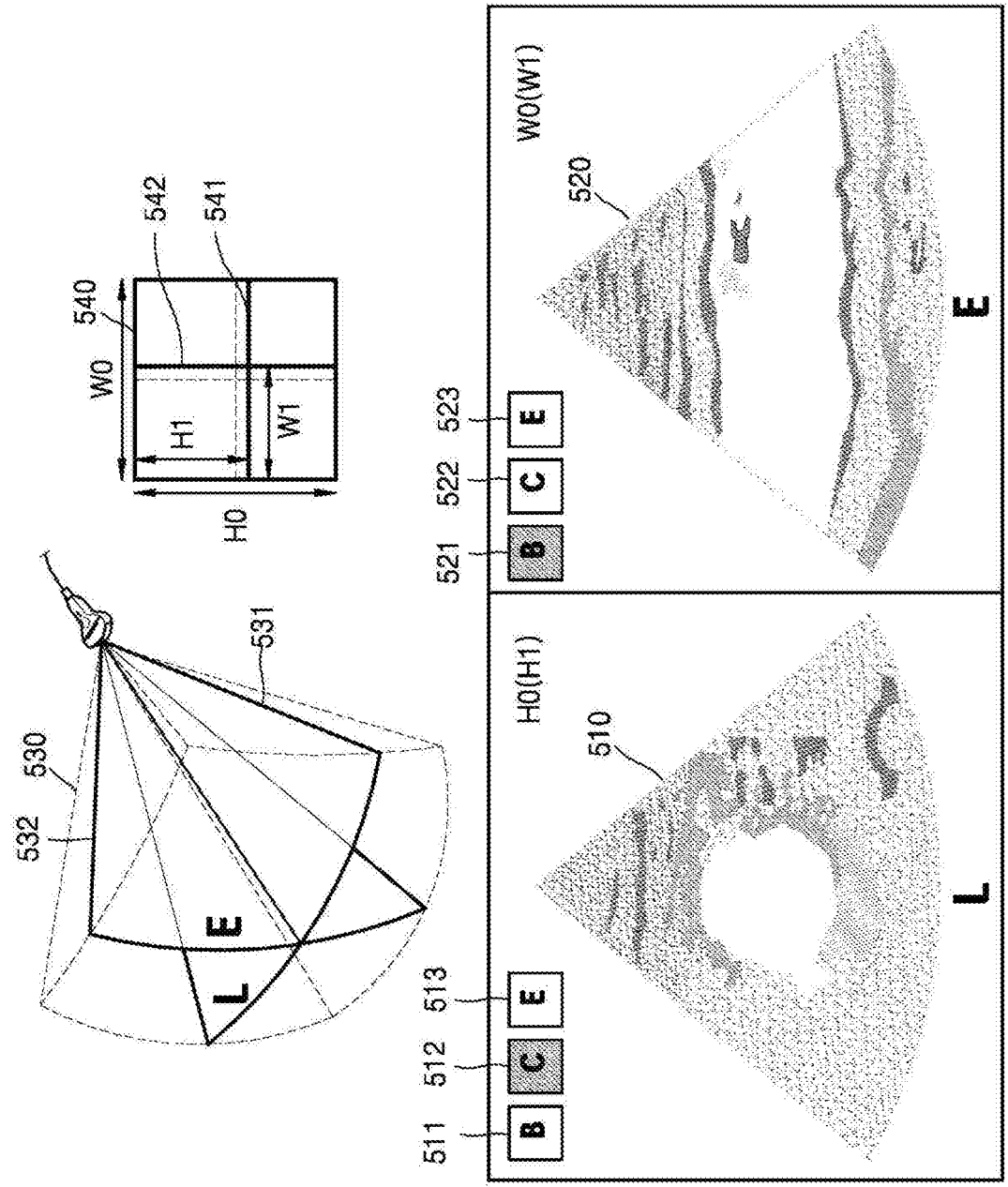

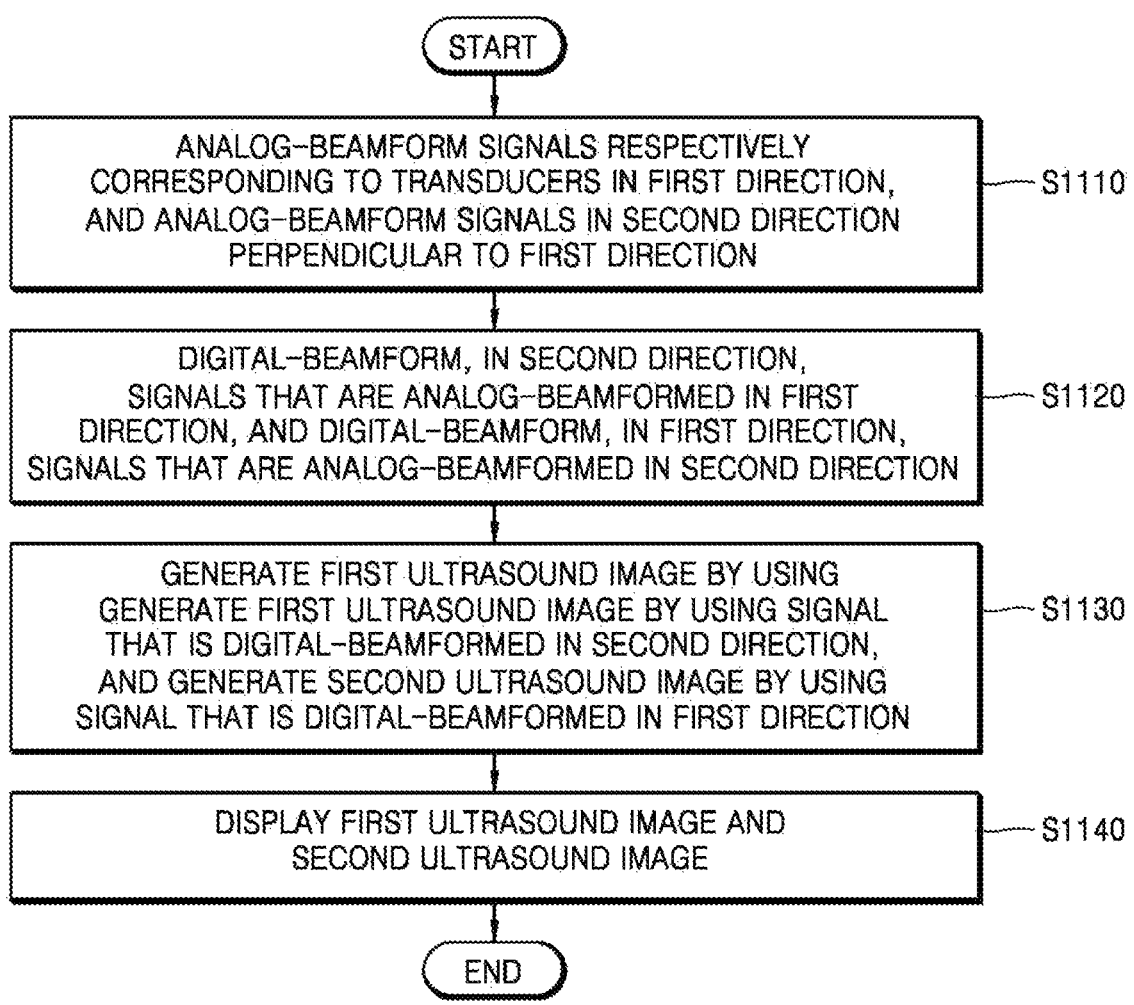

ULTRASOUND DIAGNOSIS APPARATUS AND METHOD OF OPERATING THE SAME

CROSS-REFERENCE TO RELATED APPLICATION

This application claims the benefit of Korean Patent Application No. 10-2015-0158111, filed on Nov. 11, 2015, in the Korean Intellectual Property Office, the disclosure of which is incorporated herein in its entirety by reference.

BACKGROUND

1. Field

The present disclosure relates to ultrasound diagnosis apparatuses and methods of operating the same, and more particularly, to ultrasound diagnosis apparatuses including a two-dimensional (2D) transducer array and methods of operating the same.

2. Description of the Related Art

Recently, various kinds of medical image apparatuses for visualizing information regarding biological tissue of a human body and obtaining for the purpose of early diagnosis of various kinds of diseases and operation thereon are widely in use. Representative examples of the medical image apparatuses include an ultrasound diagnosis apparatus, a computed tomography (CT) apparatus, and a magnetic resonance imaging (MRI) apparatus.

Ultrasound diagnosis apparatuses transmit ultrasound signals generated by transducers of a probe to an object and receive echo signals reflected from the object, thereby obtaining at least one image of an internal part of the object. In particular, ultrasound diagnosis apparatuses are used for medical purposes including observation of the interior of an object, detection of foreign substances, and diagnosis of damage to the object. Such ultrasound diagnosis apparatuses provide high stability, display images in real time, and are safe due to the lack of radioactive exposure, compared to X-ray apparatuses. Therefore, ultrasound imaging apparatuses are widely used together with other image diagnosis apparatuses.

Meanwhile, the ultrasound diagnosis apparatus may provide a brightness (B) mode that shows a reflective coefficient of an ultrasound signal reflected by an object by using a 2D image, a Doppler mode that shows an image of a moving object (particularly, blood flow) by using a Doppler effect, an elastic mode that shows a reaction difference between a case where compression is applied to an object and a case where compression is not applied to the object by using images, etc.

SUMMARY

Provided are ultrasound diagnosis apparatuses and methods of operating the same that may receive and focus a multi-beam in a plurality of directions with respect to signals received by a two-dimensional (2D) transducer array.

Additional aspects will be set forth in part in the description which follows and, in part, will be apparent from the description, or may be learned by practice of the presented embodiments.

According to an aspect of an embodiment, an ultrasound diagnosis apparatus includes: a two-dimensional (2D) transducer array in which a plurality of transducers that transmit/receive an ultrasound signal to/from an object are arranged in two dimensions; an analog beamformer configured to perform analog beamforming in a first direction, and perform analog beamforming in a second direction perpendicular to the first direction on signals respectively received by the plurality of transducers; and a digital beamformer configured to perform digital beamforming on the signals that are analog-beamformed in the first direction, and perform digital beamforming on the signals that are analog-beamformed in the second direction.

The analog beamformer may include: a first analog beamformer configured to perform the analog beamforming in the first direction by applying a same time delay value to transducers located at same locations in the second direction; and a second analog beamformer configured to perform the analog beamforming in the second direction by applying a same time delay value to transducers located at same locations in the first direction.

The 2D transducer array may include an M×N type 2D transducer array in which M 1D transducers are arranged in an elevation direction, and N 1D transducers are arranged in a lateral direction, the analog beamformer may be further configured to perform the analog beamforming in the lateral direction on each of the M 1D transducers arranged in the elevation direction, and perform the analog beamforming in the elevation direction on each of the N 1D transducers arranged in the lateral direction, and the digital beamformer may be further configured to perform digital beamforming on the signals that are analog-beamformed in the lateral direction, and perform digital beamforming on the signals that are analog-beamformed in the elevation direction.

A number of channels input to the digital beamformer may be M+N.

The 2D transducer array may be further configured to transmit an ultrasound signal to the object along one scan line, and receive an ultrasound signal reflected by the object, and the digital beamformer may be further configured to generate a signal corresponding to a plurality of scan lines arranged in the second direction by digital-beamforming the signals that are analog-beamformed in the first direction, and generate a signal corresponding to a plurality of scan lines arranged in the first direction by digital-beamforming the signals that are analog-beamformed in the second direction.

The apparatus may further include: an image processor configured to generate a first ultrasound image by using a signal that is obtained by digital-beamforming the signals that are analog-beamformed in the first direction, and generate a second ultrasound image by using a signal that is obtained by digital-beamforming the signals that are analog-beamformed in the second direction.

The first ultrasound image may include an image corresponding to a first cross-section of the object, and the second ultrasound image may include an image corresponding to a second cross-section of the object, and the first cross-section may be perpendicular to the second cross-section.

The first ultrasound image and the second ultrasound image may include one of a brightness (B) mode image, a color flow image, and an elastic image.

The apparatus may further include: a display configured to display the first ultrasound image and the second ultrasound image.

The display may be further configured to display at least one of a first adjustment bar that adjusts frame rates of the first ultrasound image and the second ultrasound image, and a second adjustment bar that adjusts resolutions of the first ultrasound image and the second ultrasound image.

The apparatus may further include: an input device configured to receive a user input that selects a region of interest from the first ultrasound image, wherein the display may be further configured to display the second ultrasound image including the selected region of interest.

According to an aspect of another embodiment, a method of operating an ultrasound diagnosis apparatus including a two-dimensional (2D) transducer array in which a plurality of transducers are arranged in two dimensions, the method includes: performing analog beamforming in a first direction, and performing analog beamforming in a second direction perpendicular to the first direction on signals respectively received by the plurality of transducers; and performing digital beamforming on the signals that are analog-beamformed in the first direction, and performing digital beamforming on the signals that are analog-beamformed in the second direction.

The performing of the analog beamforming in the first direction, and the performing of the analog beamforming in the second direction perpendicular to the first direction may include: performing the analog beamforming in the first direction by applying a same time delay value to transducers located at a same location in the second direction; and performing the analog beamforming in the second direction by applying a same time delay value to transducers located at a same location in the first direction.

The 2D transducer array may include an M×N type 2D transducer array in which M 1D transducers are arranged in an elevation direction, and N 1D transducers are arranged in a lateral direction, the performing of the analog beamforming in the first direction, and the performing of the analog beamforming in the second direction perpendicular to the first direction may include: performing the analog beamforming in the lateral direction on each of the M 1D transducers arranged in the elevation direction, and performing the analog beamforming in the elevation direction on each of the N 1D transducers arranged in the lateral direction, and the performing of the digital beamforming on the signals that are analog-beamformed in the first direction, and the performing of the digital beamforming on the signals that are analog-beamformed in the second direction may include: performing digital beamforming on the signals that are analog-beamformed in the lateral direction, and performing digital beamforming on the signals that are analog-beamformed in the elevation direction.

The method may further include: transmitting an ultrasound signal to the object along one scan line, and receiving an ultrasound signal reflected by the object, wherein the performing of the digital beamforming on the signals that are analog-beamformed in the first direction, and the performing of the digital beamforming on the signals that are analog-beamformed in the second direction may include: generating a signal corresponding to a plurality of scan lines arranged in the second direction by digital-beamforming the signals that are analog-beamformed in the first direction, and generating a signal corresponding to a plurality of scan lines arranged in the first direction by digital-beamforming the signals that are analog-beamformed in the second direction.

The method may further include: generating a first ultrasound image by using a signal that is obtained by digital-beamforming the signals that are analog-beamformed in the first direction, and generating a second ultrasound image by using a signal that is obtained by digital-beamforming the signals that are analog-beamformed in the second direction.

The method may further include: displaying the first ultrasound image and the second ultrasound image.

The method may further include: displaying at least one of a first adjustment bar that adjusts frame rates of the first ultrasound image and the second ultrasound image, and a second adjustment bar that adjusts resolutions of the first ultrasound image and the second ultrasound image.

The method may further include: receiving a user input that selects a region of interest from the first ultrasound image; and displaying the second ultrasound image including the selected region of interest.

According to an embodiment, a multi-beam may be implemented in the first direction and the second direction without an error.

According to an embodiment, a multi-beam may be implemented in the first direction and the second direction, so that a frame rate of an ultrasound image may be increased.

According to an embodiment, a number of cables connecting an analog beamformer with a digital beamformer may be reduced.

According to an embodiment, an amount of operations by analog beamforming may be reduced.

BRIEF DESCRIPTION OF THE DRAWINGS

These and/or other aspects will become apparent and more readily appreciated from the following description of the embodiments, taken in conjunction with the accompanying drawings in which:

FIGS. 8A to 8D are diagrams illustrating an example in which a first ultrasound image and a second ultrasound image are displayed on a display according to an embodiment;

FIG. 12 is a flowchart illustrating a method of operating an ultrasound diagnosis apparatus according to an embodiment.

DETAILED DESCRIPTION

Figure 1:
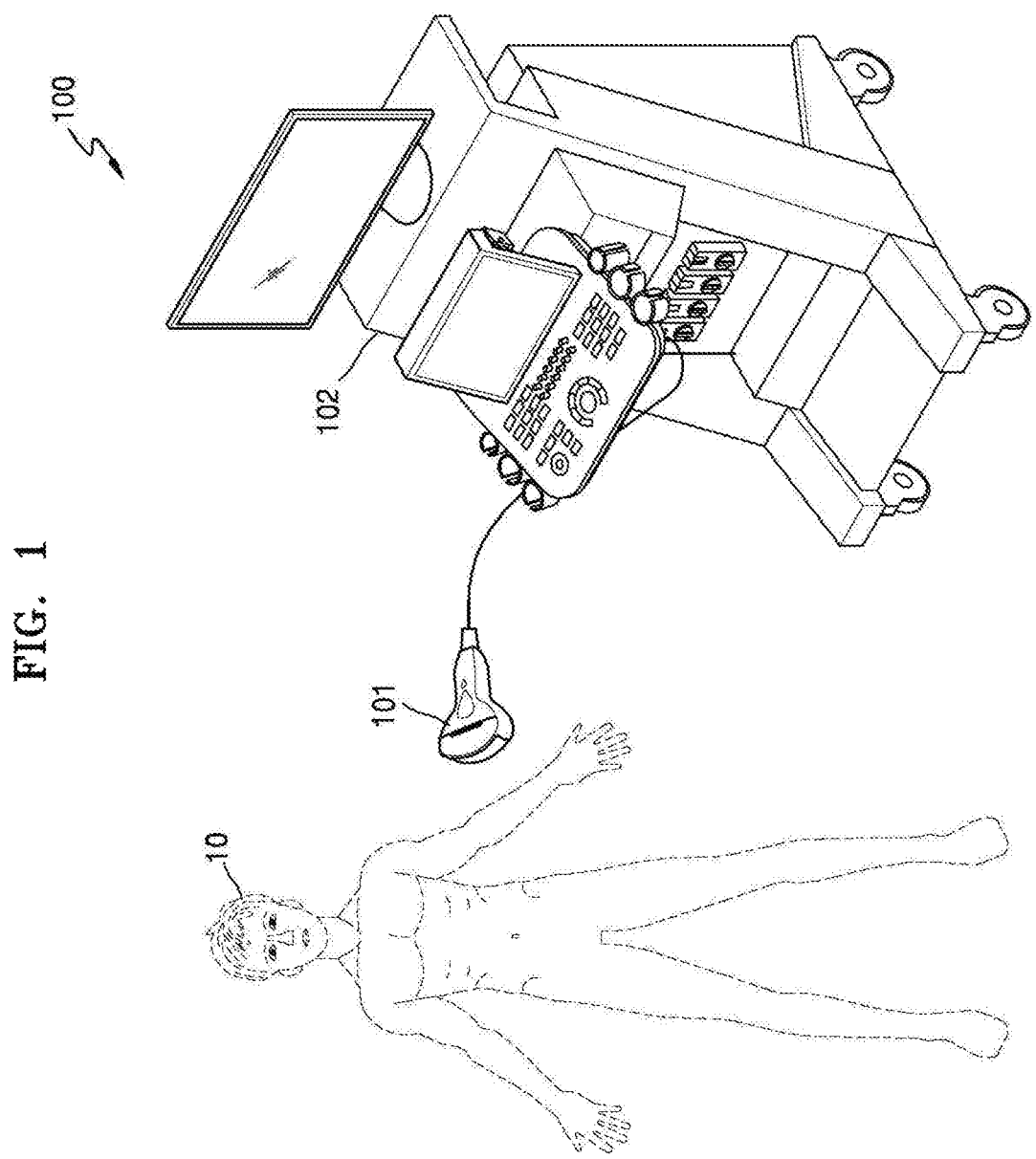
FIG. 1 is a view illustrating an ultrasound diagnosis apparatus according to an embodiment.

The terms used in this specification are those general terms currently widely used in the art in consideration of functions regarding the inventive concept, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used herein have to be defined based on the meaning of the terms together with the description throughout the specification.

Throughout the specification, it will also be understood that when a component "includes" an element, unless there is another opposite description thereto, it should be understood that the component does not exclude another element and may further include another element. In addition, terms such as " . . . unit", " . . . module", or the like refer to units that perform at least one function or operation, and the units may be implemented as hardware or software or as a combination of hardware and software.

Throughout the specification, an "image" may denote multi-dimensional data including discrete image elements. For example, an image may include a medical image (an ultrasound image, a CT image, an MR image), etc. of an object obtained by an ultrasound apparatus, a CT apparatus, and an MRI apparatus, but is not limited thereto.

Furthermore, an "object" may be a human, an animal, or a part of a human or animal. For example, the object may be an organ (e.g., the liver, the heart, the womb, the brain, a breast, or the abdomen), a blood vessel, or a combination thereof. Also, the object may be a phantom. The phantom means a material having a density, an effective atomic number, and a volume that are approximately the same as those of an organism. For example, the phantom may be a spherical phantom having properties similar to a human body.

An ultrasound image may denote an image obtained by irradiating an ultrasound signal generated from a transducer of a probe to an object and receiving information of an echo signal reflected by the object. Also, an ultrasound image may be implemented variously. For example, an ultrasound image may be at least one of an amplitude (A) mode image, a brightness (B) mode image, a color (C) mode image, and a Doppler (D) mode image. Also, according to an embodiment, an ultrasound image may be a two-dimensional (2D) image or a three-dimensional (3D) image.

Throughout the specification, a "user" may be, but is not limited to, a medical expert, for example, a medical doctor, a nurse, a medical laboratory technologist, or a medical imaging expert, or a technician who repairs medical apparatuses.

Reference will now be made in detail to embodiments, examples of which are illustrated in the accompanying drawings. In this regard, the present embodiments may have different forms and should not be construed as being limited to the descriptions set forth herein.

Figure 2:
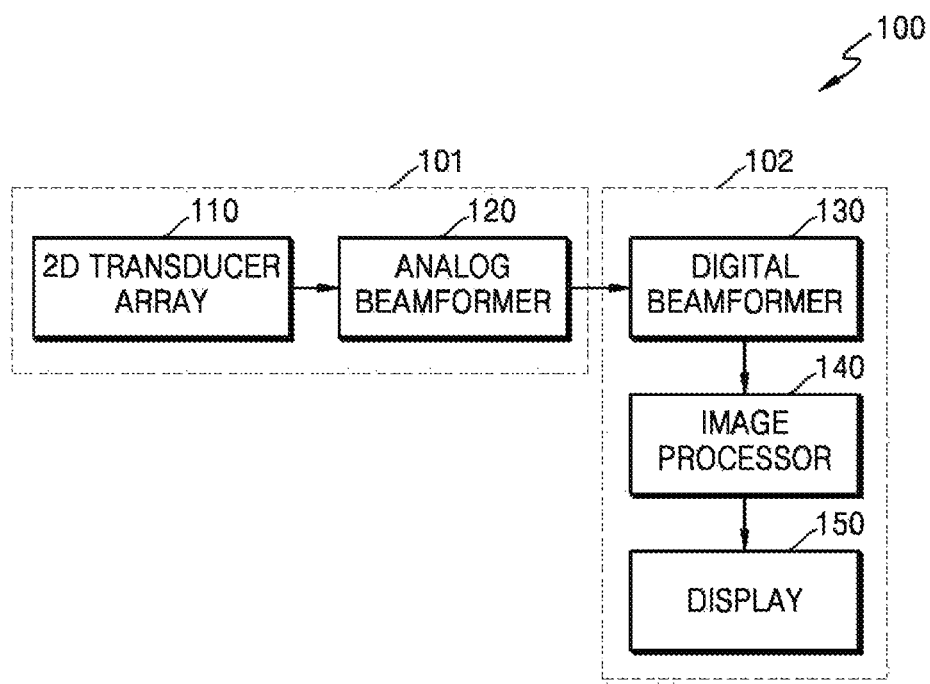
FIG. 2 is a block diagram illustrating an ultrasound diagnosis apparatus according to an embodiment.

FIG. 1 is a view illustrating an ultrasound diagnosis apparatus 100 according to an embodiment, and FIG. 2 is a block diagram illustrating the ultrasound diagnosis apparatus 100 according to an embodiment. Referring to FIGS. 1 and 2, the ultrasound diagnosis apparatus 100 may include a main body 102, and a probe 101 connected to the main body 102.

The probe 101 according to an embodiment may include a 2D transducer array 110 in which a plurality of transducers are arranged in two dimensions, and an analog beamformer 120 connected to the 2D transducer array 110.

For example, each of the plurality of transducers included in the 2D transducer array 110 may convert an input electric signal into an ultrasound signal, and transmit the converted ultrasound signal to an object 10. Also, each of the plurality of transducers may receive an ultrasound signal reflected by the object 10, convert the received ultrasound signal into an electric signal, and transmit the same to the analog beamformer 120.

The analog beamformer 120 according to an embodiment may include a first analog beamformer and a second analog beamformer. The first analog beamformer may perform analog beamforming on signals respectively received by the transducers in a first direction, and the second analog beamformer may perform analog beamforming in a second direction perpendicular to the first direction.

Also, the ultrasound diagnosis apparatus 100 may include a digital beamformer 130, an image processor 140, and a display 150. The digital beamformer 130, the image processor 140, and the display 150 may be included in the main body 102, but are not limited thereto and may be implemented as separate modules independent of the main body 102 and detachable from the main body 102.

The digital beamformer 130 according to an embodiment may be connected with the analog beamformer 120 included in the probe 101 by using a cable and may receive analog-beamformed signals from the analog beamformer 120.

For example, the digital beamformer 130 may include a first digital beamformer and a second digital beamformer. The first digital beamformer digital-beamforms a signal that is analog-beamformed in the first direction, and the second digital beamformer digital-beamforms a signal that is analog-beamformed in the second direction.

The image processor 140 may generate an ultrasound image based on a beamformed signal. An ultrasound image according to an embodiment may include a first ultrasound image and a second ultrasound image. The first ultrasound image may be an image generated based on signals obtained by digital-beamforming signals that are analog-beamformed in the first direction, and the second ultrasound image may be an image generated based on signals obtained by digital-beamforming signals that are analog-beamformed in the second direction. The first ultrasound image and the second ultrasound image may be images corresponding to cross-sections perpendicular to each other.

The display 150 may display the generated first ultrasound image and second ultrasound image. The display 150 may display not only an ultrasound image, but also various pieces of information processed by the ultrasound diagnosis apparatus 100 on a screen image via a graphical user interface (GUI). In addition, the ultrasound diagnosis apparatus 100 may include two or more displays 150 according to embodiments.

Figure 3:
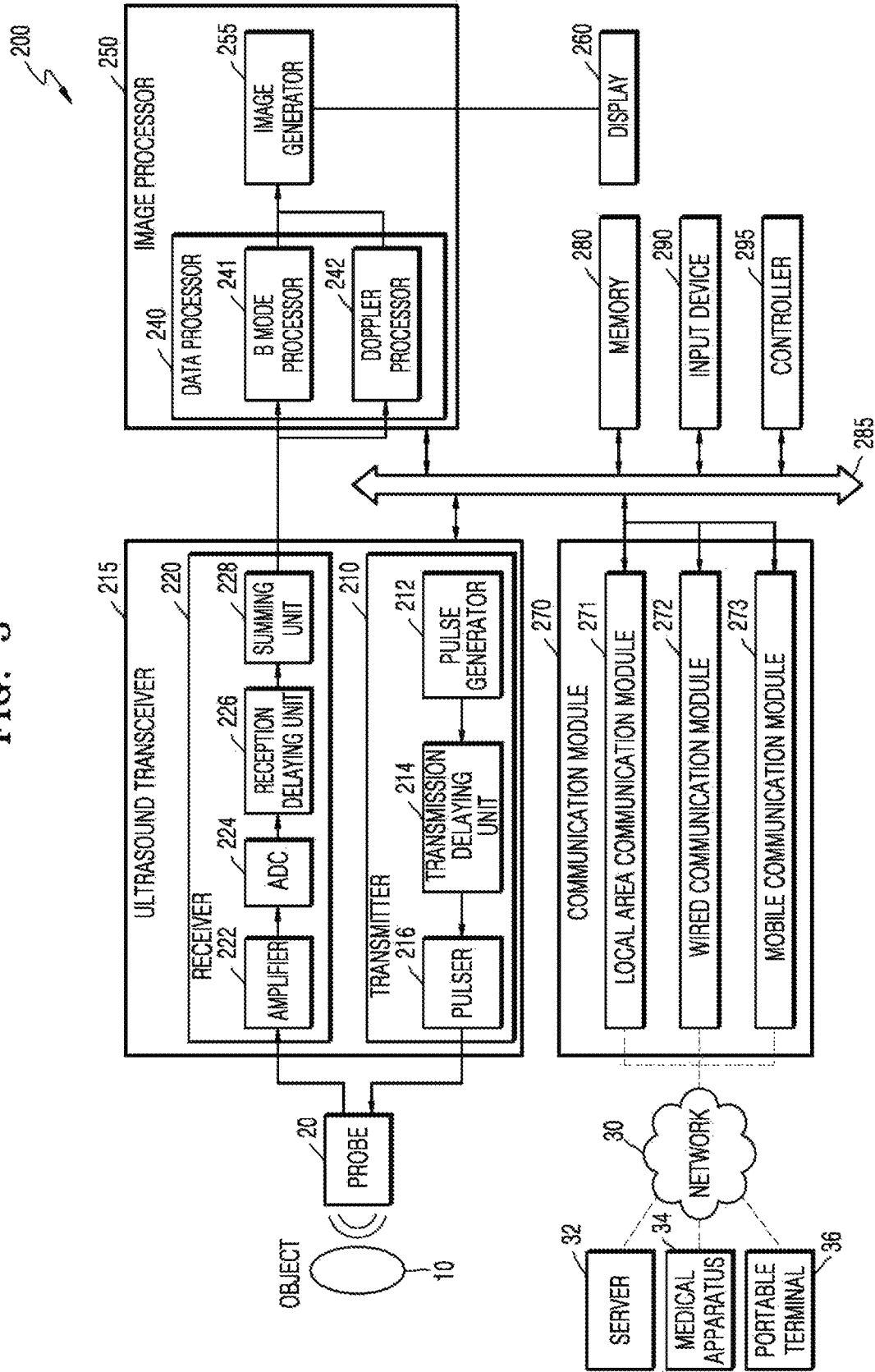
FIG. 3 is a block diagram illustrating an ultrasound diagnosis apparatus according to an embodiment.

FIG. 3 is a block diagram illustrating an ultrasound diagnosis apparatus 200 according to an embodiment.

Referring to FIG. 3, the ultrasound diagnosis apparatus 200 may include a probe 20, an ultrasound transceiver 215, an image processor 250, a communication module 260, a memory 280, an input device 290, and a controller 295. The above components may be connected with each other via a bus 285.

Meanwhile, the 2D transducer array 110 of FIG. 2 may be a component corresponding to the probe 20 of FIG. 3. The analog beamformer 120 and the digital beamformer 130 of FIG. 2 may be a component corresponding to an ultrasound receiver 220 of FIG. 3. The image processor 140 of FIG. 2 may be a component corresponding to the image processor 250 of FIG. 3. The display 150 of FIG. 2 may be a component corresponding to the display 260 of FIG. 3. Accordingly, the descriptions of the components 110, 120, 130, 140, and 150 described in FIG. 2 are equally applicable to the corresponding components 20, 220, 250, and 260 of FIG. 3, respectively, and repeated descriptions of FIG. 2 are omitted.

In some embodiments, the ultrasound diagnosis apparatus 200 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 20 transmits ultrasound waves to an object 10 in response to a driving signal applied by the ultrasound transceiver 215 and receives echo signals reflected by the object 10. The probe 20 includes a plurality of transducers, and the plurality of transducers oscillate in response to electric signals and generate acoustic energy, that is, ultrasound waves. Furthermore, the probe 20 may be connected to the main body of the ultrasound diagnosis apparatus 200 by wire or wirelessly, and according to embodiments, the ultrasound diagnosis apparatus 200 may include a plurality of probes 20.

A transmitter 210 supplies a driving signal to the probe 20. The transmitter 110 includes a pulse generator 212, a transmission delaying unit 214, and a pulser 216. The pulse generator 212 generates pulses for forming transmission ultrasound waves based on a predetermined pulse repetition frequency (PRF), and the transmission delaying unit 214 delays the pulses by delay times necessary for determining transmission directionality. The pulses which have been delayed correspond to a plurality of piezoelectric vibrators included in the probe 20, respectively. The pulser 216 applies a driving signal (or a driving pulse) to the probe 20 based on timing corresponding to each of the pulses which have been delayed.

A receiver 220 generates ultrasound data by processing echo signals received from the probe 20. The receiver 120 may include an amplifier 222, an analog-to-digital converter (ADC) 224, a reception delaying unit 226, and a summing unit 228. The amplifier 222 amplifies echo signals in each channel, and the ADC 224 performs analog-to-digital conversion with respect to the amplified echo signals. The reception delaying unit 226 delays digital echo signals output by the ADC 1124 by delay times necessary for determining reception directionality, and the summing unit 228 generates ultrasound data by summing the echo signals processed by the reception delaying unit 1126. In some embodiments, the receiver 220 may not include the amplifier 222. In other words, if the sensitivity of the probe 20 or the capability of the ADC 224 to process bits is enhanced, the amplifier 222 may be omitted.

The image processor 250 generates an ultrasound image by scan-converting ultrasound data generated by the ultrasound transceiver 215 and displays the ultrasound image.

The image processor 120 extracts B mode components from ultrasound data and processes the B mode components. The image processor 120 may generate an ultrasound image indicating signal intensities as brightness based on the extracted B mode components.

The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood (also referred to as a color flow image), a tissue Doppler image showing a movement of tissue, or a spectral Doppler image showing a moving speed of an object as a waveform.

A B mode processor 241 extracts B mode components from ultrasound data and processes the B mode components. An image generator 255 may generate an ultrasound image indicating signal intensities as brightness based on the extracted B mode components 241.

Similarly, a Doppler processor 242 may extract Doppler components from ultrasound data, and the image generator 255 may generate a Doppler image indicating a movement of an object as colors or waveforms based on the extracted Doppler components.

According to an embodiment, the image generator 255 may generate a three-dimensional (3D) ultrasound image via volume-rendering with respect to volume data and may also generate an elasticity image by imaging deformation of the object 10 due to pressure.

Furthermore, the image generator 255 may display various pieces of additional information in an ultrasound image by using text and graphics. In addition, the generated ultrasound image may be stored in the memory 280.

The display 260 may include at least one of a liquid crystal display, a thin film transistor-liquid crystal display, an organic light-emitting diode, a flexible display, a 3D display, and an electrophoretic display.

Also, in the case where the display 260 and a user interface form a layer structure and are configured as a touchscreen, the display 260 may be used as not only an output unit but also an input unit that may receive information by a user's touch.

The touchscreen may be configured to detect not only a touch input location and a touched area but also a touch pressure. Also, the touchscreen may be configured to detect not only a real-touch but also a proximity touch.

The communication module 270 is connected to a network 30 by wire or wirelessly to communicate with an external device or a server. The communication module 270 may exchange data with a hospital server or another medical apparatus in a hospital, which is connected thereto via a PACS. Furthermore, the communication module 170 may perform data communication according to the digital imaging and communications in medicine (DICOM) standard.

The communication module 270 may transmit or receive data related to diagnosis of an object, e.g., an ultrasound image, ultrasound data, and Doppler data of the object, via the network 30 and may also transmit or receive medical images captured by another medical apparatus, e.g., a computed tomography (CT) apparatus, a magnetic resonance imaging (MRI) apparatus, or an X-ray apparatus. Furthermore, the communication module 270 may receive information about a diagnosis history or medical treatment schedule of a patient from a server and utilizes the received information to diagnose the patient. Furthermore, the communication module 270 may perform data communication not only with a server or a medical apparatus in a hospital, but also with a portable terminal of a medical doctor or patient.

The communication module 270 is connected to the network 30 by wire or wirelessly to exchange data with a server 32, a medical apparatus 34, or a portable terminal 36. The communication module 270 may include one or more components for communication with external devices. For example, the communication module 1300 may include a local area communication module 271, a wired communication module 272, and a mobile communication module 273.

The local area communication module 271 refers to a module for local area communication within a predetermined distance. Examples of local area communication techniques according to an embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 272 refers to a module for communication using electric signals or optical signals. Examples of wired communication techniques according to an embodiment may include communication via a twisted pair cable, a coaxial cable, an optical fiber cable, and an Ethernet cable.

The mobile communication module 273 transmits or receives wireless signals to or from at least one selected from a base station, an external terminal, and a server on a mobile communication network. The wireless signals may be voice call signals, video call signals, or various types of data for transmission and reception of text/multimedia messages.

The memory 280 stores various data processed by the ultrasound diagnosis apparatus 200. For example, the memory 180 may store medical data related to diagnosis of an object, such as ultrasound data and an ultrasound image that are input or output, and may also store algorithms or programs which are to be executed in the ultrasound diagnosis apparatus 200.

The memory 280 may be any of various storage media, e.g., a flash memory, a hard disk drive, EEPROM, etc. Furthermore, the ultrasound diagnosis apparatus 100 may utilize web storage or a cloud server that performs the storage function of the memory 280 online.

The input device 290 refers to a means via which a user inputs data for controlling the ultrasound diagnosis apparatus 50. The input device 290 may include hardware components, such as a keypad, a mouse, a touch pad, a touch screen, and a jog switch. Also, the input device 290 may recognize a user's fingerprint by including a fingerprint recognition sensor. The input device 290 may further include any of various other input units including an electrocardiogram (ECG) measuring module, a respiration measuring module, a voice recognition sensor, a gesture recognition sensor, an iris recognition sensor, a depth sensor, a distance sensor, etc. In particular, the input device 290 may include a touchscreen in which a touchpad and the above-described display 260 form a layered structure.

In this case, the ultrasound diagnosis apparatus 200 according to an embodiment may display an ultrasound image of a predetermined mode and a control panel for an ultrasound image on the touchscreen. Also, the ultrasound diagnosis apparatus 200 may detect a user's touch gesture with respect to an ultrasound image via the touchscreen.

The ultrasound diagnosis apparatus 200 according to an embodiment may physically include some buttons frequently used by a user from among buttons included in a control panel of a general ultrasound apparatus, and provide the rest of the buttons in the form of a graphical user interface (GUI) via the touchscreen.

The controller 295 may control all operations of the ultrasound diagnosis apparatus 200. In other words, the controller 295 may control operations among the probe 20, the ultrasound transceiver 200, the image processor 250, the communication module 270, the memory 280, and the input device 290 shown in FIG. 3.

All or some of the probe 20, the ultrasound transceiver 215, the image processor 250, the display 240, the communication module 270, the memory 280, the input device 290, and the controller 295 may be implemented as software modules. However, embodiments of the present invention are not limited thereto, and some of the components stated above may be implemented as hardware modules. Also, at least one of the ultrasound transmission/reception unit 215, the image processor 250, and the communication module 270 may be included in the control unit 295; however, the inventive concept is not limited thereto.

Figure 4:
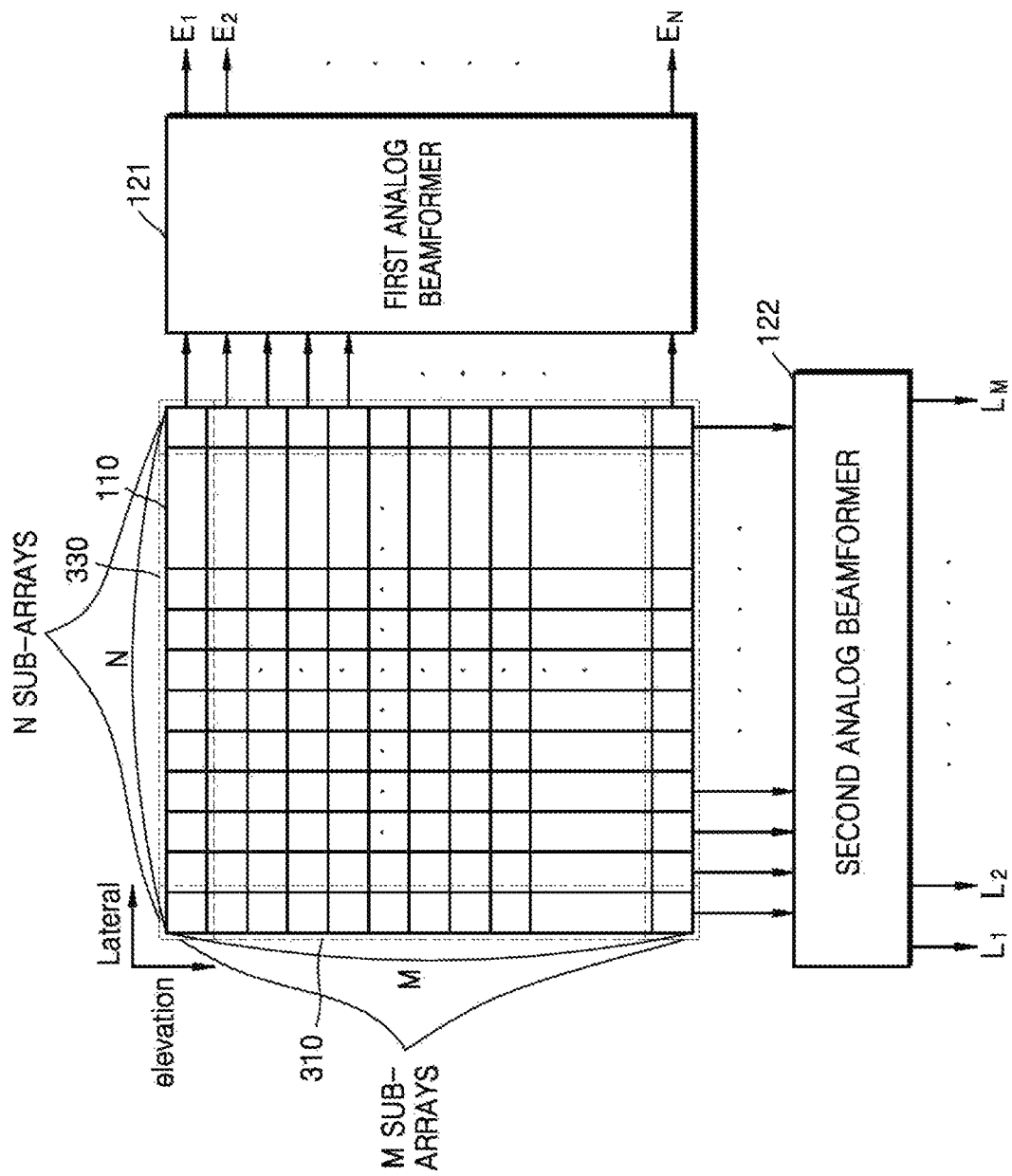
FIG. 4 is a view illustrating a probe according to an embodiment.

FIG. 4 is a view illustrating a probe 101 according to an embodiment.

Referring to FIG. 4, the probe 101 according to an embodiment may include a 2D transducer array 110, a first analog beamformer 121, and a second analog beamformer 122.

The 2D transducer array 110 may have a form in which a plurality of transducers transmitting/receiving an ultrasound signal to/from an object are arranged in two dimensions. For example, the 2D transducer array 110 may be an M×N type 2D transducer array in which M transducers are arranged in an elevation direction, and N transducers are arranged in a lateral direction. In this case, M and N may be integers equal to or greater than 1, and M and N may the same numbers.

An electric signal may be input to each of the plurality of transducers included in the 2D transducer array 110. When an electric signal is input, the transducers may convert the electric signal into an ultrasound signal, and transmit the converted ultrasound signal to an object. Also, the transducers may receive an ultrasound signal reflected by the object, and convert the received ultrasound signal into an electric signal.

The first analog beamformer 121 according to an embodiment may perform analog beamforming in the first direction on signals respectively corresponding to the plurality of transducers. Also, the second analog beamformer 122 according to an embodiment may perform analog beamforming in the second direction perpendicular to the first direction on signals respectively corresponding to the plurality of transducers.

For example, in the case where the 2D transducer array 110 is an M×N type 2D transducer array in which M transducers are arranged in an elevation direction, and N transducers are arranged in a lateral direction as described above, the first direction may be the elevation direction or the lateral direction. In the case where the first direction is the elevation direction, the second direction may be the lateral direction. In the case where the first direction is the lateral direction, the second direction may be the elevation direction. However, the inventive concept is not limited thereto.

Meanwhile, before analog beamforming is performed on signals respectively corresponding to the transducers, the signals respectively corresponding to the transducers may be transmitted to a reception signal processor (not shown). The reception signal processor (not shown) may perform predetermined processing on a signal received from the transducers. For example, the reception signal processor (not shown) may include a low noise amplifier (LNA)(not shown) that reduces noise of an analog signal received from the transducers, and a variable gain amplifier (VGA)(not shown) that controls a gain value depending on an input value. In this case, the reception signal processor may include a time gain compensation (TGC) that compensates for a gain depending on a distance from a focus point, but is not limited thereto.

Referring to FIG. 4 again, analog beamforming according to an embodiment is described. Hereinafter, for convenience of description, description is made on the assumption that the 2D transducer array 110 is an M×N type transducer array, the first direction is the elevation direction, and the second direction is the lateral direction, but is not limited thereto.

For example, in the case where M transducers arranged in a line in the elevation direction are grouped as one sub-array, the 2D transducer array 110 may include N sub-arrays arranged in the lateral direction. Also, the ultrasound diagnosis apparatus 100 may further include a switching unit (not shown), and the switching unit (not shown) may perform switching so that a signal may be received in the first analog beamformer 121 for each sub-array (the first to N-th sub-arrays). Accordingly, the first analog beamformer 121 may perform analog beamforming on the N sub-arrays on a sub-array basis.

For example, in the case where first to M-th transducers forming a first sub-array 310 receive an ultrasound signal reflected by an object, times at which ultrasound signals reflected by a focus point reach respective transducers differ due to a difference in a distance between each of the transducers forming the first sub-array 310 and the focus point. Therefore, the first analog beamformer 121 may delay signals respectively corresponding to the first to M-th transducers by a delay time (a time delay value) calculated by taking into account a difference in a distance between each of the first to M-th transducers and the focus point, and then sum the delayed signals as one signal. Accordingly, the first analog beamformer 121 may generate an analog signal $E_1$ by performing analog beamforming on the first sub-array 310.

Also, the first analog beamformer 121 may generate analog signals $E_2$, $E_3$, . . . , $E_N$ by performing analog beamforming on each of the second to N-th sub-arrays in the same method that has been performed on the first sub-array 310. The first analog beamformer 121 is a beamformer that performs analog beamforming in the elevation direction, and outputs N analog-beamformed signals by performing analog beamforming on each of the N sub-arrays. Therefore, the first analog beamformer 121 generates the analog signals $E_1, \ldots, E_N$.

Likewise, the second analog beamformer is a beamformer that performs analog beamforming in the lateral direction, and outputs M analog-beamformed signals by performing analog beamforming on each of M sub-arrays.

In this case, time delay values respectively applied to N sub-arrays may be the same. For example, the same time delay value may be applied to transducers located on the same location in the lateral direction in each of the N sub-arrays, but is not limited thereto (the same delay value may be applied and the same delay value may not be always applied).

Meanwhile, in the case where N transducers arranged in a line in the lateral direction are grouped as one sub-array, the 2D transducer array 110 may include M sub-arrays arranged in the elevation direction.

The switching unit (not shown) may perform switching so that a signal may be received in the second analog beamformer 122 for each sub-array ((N+1)-th to (N+M)-th sub-arrays). Accordingly, the second analog beamformer 122 may perform analog beamforming on the M sub-arrays on a sub-array basis.

In the case where the first to N-th transducers forming an (N+1)-th sub-array 330 receives an ultrasound signal reflected by an object, times at which ultrasound signals reflected by a focus point reach respective transducers differ due to a difference in a distance between each of the transducers and the focus point.

Therefore, the second analog beamformer 122 delays signals respectively corresponding to the first to N-th transducers by a delay time (a time delay value) calculated by taking into account a difference in a distance between each of the first to N-th transducers forming the (N+1)-th sub-array 330 and the focus point, and then sums the delayed signals as one signal. Accordingly, the second analog beamformer 122 may generate an analog signal $L_1$ by performing analog beamforming on the (N+1)-th sub-array 330.

Also, the second analog beamformer 122 may generate analog signals $L_2$, $L_3$, . . . , $L_{NA}$ by performing analog beamforming on each of (N+2)-th to (N+M)-th sub-arrays in the same method that has been performed on the (N+1)-th sub-array 330.

In this case, time delay values respectively applied to the (N+1)-th to (N+M)-th sub-arrays may be the same. For example, the same time delay value may be applied to transducers located on the same location in the elevation direction in each of the sub-arrays, but is not limited thereto.

The first analog beamformer 121 and the second analog beamformer 122 according to an embodiment may transmit (N+M) analog signals to the digital beamformer 130 via a cable having (N+M) channels.

Meanwhile, in FIG. 4, the description has been made on the assumption that the first direction is the elevation direction, and the second direction is the lateral direction, but in the case where the 2D transducer array is an M×N square type transducer array, the first direction may be a first diagonal direction of the 2D transducer array, and the second direction may be a second diagonal direction of the 2D transducer array. In this case, the first analog beamformer 121 may perform analog beamforming in the first diagonal direction, and the second analog beamformer 122 may perform analog beamforming in the second diagonal direction.

Figure 5:
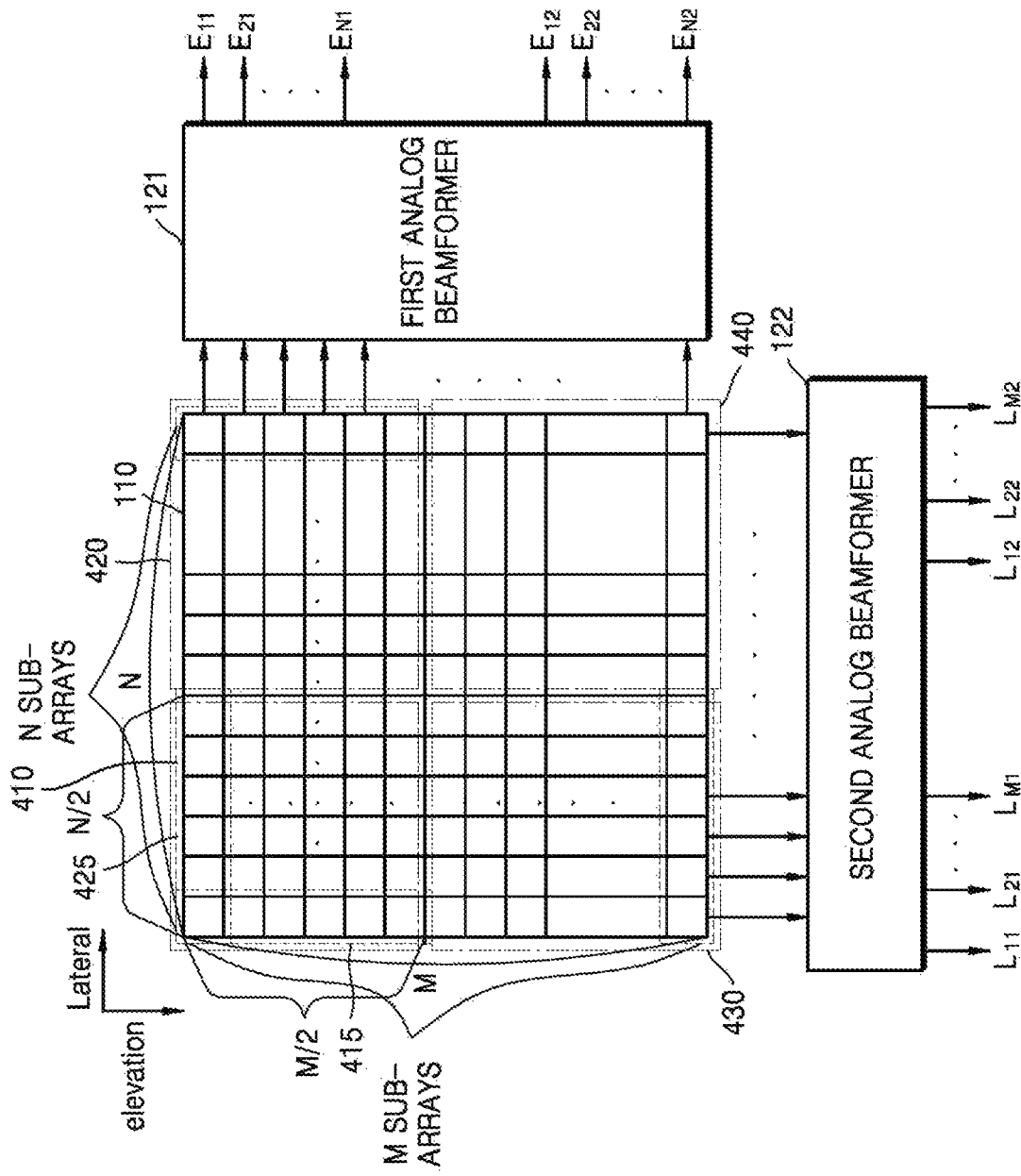
FIG. 5 is a view for explaining analog beamforming according to an embodiment.

FIG. 5 is a view for explaining analog beamforming according to an embodiment. In FIG. 5, for convenience of description, description is made on the assumption that the 2D transducer array 110 is an M×N type transducer array, the first direction is the elevation direction, and the second direction is the lateral direction, but is not limited thereto.

According to an embodiment, the 2D transducer array 110 may be divided into K regions (K is an integer greater than 1), and in each of the K regions, transducers arranged in a line in the elevation direction may be configured as one sub-array, or transducers arranged in a line in the lateral direction may be configured as one sub-array.

For example, as illustrated in FIG. 5, the ultrasound diagnosis apparatus 100 may divide the 2D transducer array 110 into four regions 410, 420, 430, and 440 and perform analog beamforming. In this case, in the case where M/2 transducers arranged in a line in the elevation direction in the first region 410 and the second region 420 are grouped as one sub-array, the first region 410 and the second region 420 may include N sub-arrays arranged in the lateral direction. As described with reference to FIG. 4, the ultrasound diagnosis apparatus 100 may further include the switching unit (not shown), and the switching unit (not shown) may perform switching so that a signal may be received in the first analog beamformer 121 for each sub-array. Accordingly, the first analog beamformer 121 may perform analog beamforming on N sub-arrays for each sub-array.

The first analog beamformer 121 may delay signals respectively corresponding to the M/2 transducers by a time delay value calculated by taking into account a difference in a distance between each of the M/2 transducers forming the sub-array 415 and the focus point, and then sum the delayed signals as one signal. Accordingly, the first analog beamformer 121 may generate an analog signal $E_{11}$ by performing analog beamforming on the sub-array 415. Also, the first analog beamformer 121 may generate analog signals $E_{21}, \ldots, E_{N1}$ by performing analog beamforming on each of the rest of sub-arrays included in the first region 410 and the second region 420 by using the same method that has been performed on the sub-array 415.

Also, in the case where M/2 transducers arranged in a line in the elevation direction in the third region 430 and the fourth region 440 are grouped as one sub-array, the third region 430 and the fourth region 440 may include N sub-arrays arranged in the lateral direction. The first analog beamformer 121 may generate analog signals $E_{12}$, $E_{22}, \ldots, E_{N2}$ by equally performing analog beamforming on N sub-arrays by using the same method as described above.

Also, in the case where N/2 transducers arranged in a line in the lateral direction in the first region 410 and the third region 430 are grouped as one sub-array, the first region 410 and the third region 430 may include M sub-arrays arranged in the elevation direction. The switching unit (not shown) may perform switching so that a signal may be received in the second analog beamformer 122 for each sub-array. Accordingly, the second analog beamformer 122 may perform analog beamforming on M sub-arrays on each sub-array basis.

The second analog beamformer 122 may delay signals respectively corresponding to transducers (N/2 transducers) by a time delay value calculated by taking into account a difference in a distance between each of N/2 transducers forming the sub-array 425 and the focus point, and then sum the delayed signals as one signal. Accordingly, the second analog beamformer 122 may generate an analog signal $L_{11}$ by performing analog beamforming on the sub-array 425. Also, the second analog beamformer 122 may generate analog signals $L_{21}, \ldots, L_{M1}$ by performing analog beamforming on each of the rest of sub-arrays included in the first region 410 and the third region 430 by using the same method that has been performed on the sub-array 415.

Also, in the case where N/2 transducers arranged in a line in the lateral direction in the second region 420 and the fourth region 440 are grouped as one sub-array, the second region 420 and the fourth region 440 may include M sub-arrays arranged in the elevation direction. The second analog beamformer 122 may generate analog signals $L_{12}$, $L_{22}, \ldots, L_{M2}$ by equally performing analog beamforming on M sub-arrays by using the same method as described above.

As described in FIG. 5, in the case of dividing the 2D transducer array into four regions and performing analog beamforming, an amount of operation for the analog beamforming may reduce compared with the case of not dividing the region of the 2D transducer array. Also, a number of signals generated as a result of analog beamforming becomes two times greater than the case of not dividing the region, so that a number of channels connecting the analog beamformer with the digital beamformer may increase two times.

Meanwhile, though FIG. 5 illustrates and describes a method of dividing the 2D transducer array into four regions and performing analog beamforming, the method is not limited thereto, and the ultrasound diagnosis apparatus 100 according to an embodiment may divide the 2D transducer array 110 into K regions (K is an integer greater than 1), and configure transducer arrays arranged in a line in the elevation direction as one sub-array, or configure transducer arrays arranged in a line in the lateral direction as one sub-array.

Also, though FIG. 5 describes dividing the 2D transducer array 110 into regions in the lateral direction and the elevation direction, the ultrasound diagnosis apparatus 100 according to an embodiment is not limited thereto and may divide the 2D transducer array 110 into only one of the lateral direction and the elevation direction and perform analog beamforming.

Figure 6:
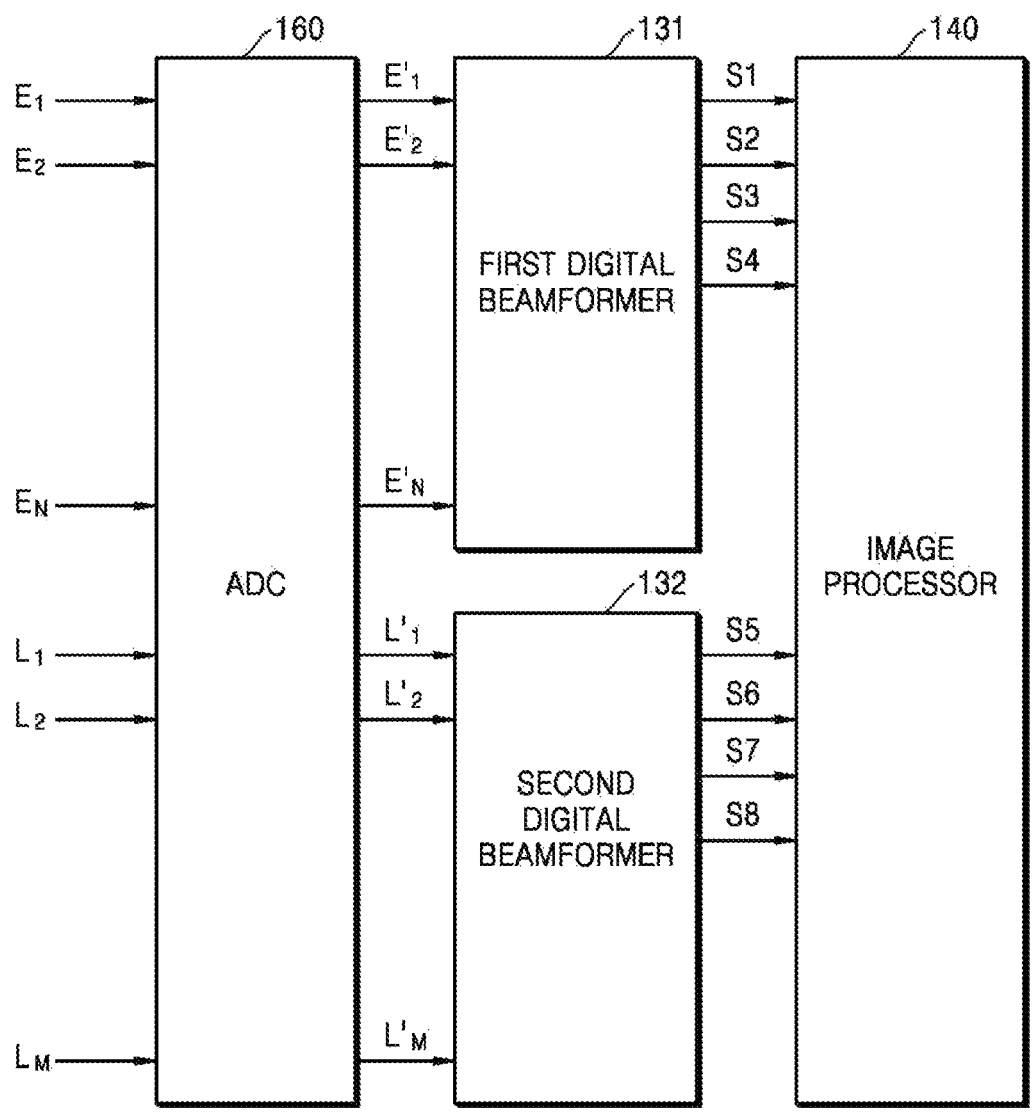
FIG. 6 is a block diagram illustrating a main body of an ultrasound diagnosis apparatus according to an embodiment.
Figure 7:
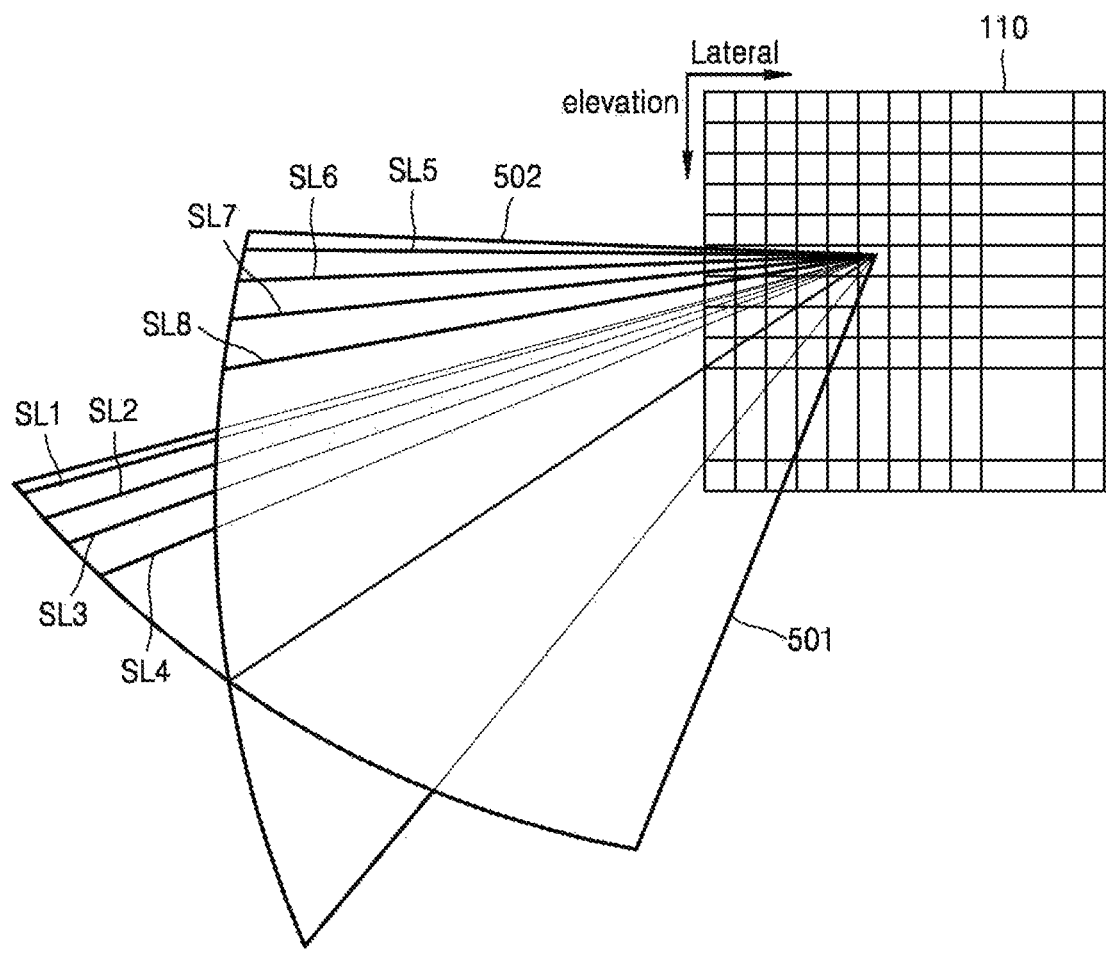
FIG. 7 is a view for explaining a method of generating an ultrasound image in an ultrasound diagnosis apparatus according to an embodiment.

FIG. 6 is a block diagram illustrating a main body 102 of an ultrasound diagnosis apparatus according to an embodiment, and FIG. 7 is a view for explaining a method of generating an ultrasound image in an ultrasound diagnosis apparatus according to an embodiment.

Referring to FIG. 6, the main body 102 may include an analog-to-digital converter (ADC) 160, a first digital beamformer 131, a second digital beamformer 132, and an image processor 140.

The main body 102 according to an embodiment may be connected with the probe 101 by using a cable and receive analog-beamformed signals. For example, the main body 102 may receive analog signals $E_1, E_2, \ldots, E_N$ that are analog-beamformed in the elevation direction, and analog signals $L_1, L_2, \ldots, L_M$ that are analog-beamformed in the lateral direction.

The ADC 160 may convert a plurality of analog signals generated by the analog beamformers 121 and 122 into digital signals.

The first digital beamformer 131 may receive digital signals $E'_1, E'_2, \ldots, E'_N$ into which signals that are analog-beamformed in the elevation direction have been converted, and perform digital beamforming. The first digital beamformer 131 may delay each of the digital signals $E'_1$, $E'_2, \ldots, E'_N$ by a time delay value calculated by taking into account a difference in a distance between each of first to N-th sub-arrays arranged in the lateral direction and a focus point, and then sum the delayed signals as one signal.

In this case, since one sub-array includes a plurality of transducers, a distance between a sub-array and the focus point may be calculated based on various criteria. For example, a distance between a sub-array and the focus point may be calculated by using one of a distance between the focus point and a transducer located closest to the focus point from among transducers included in the sub-array, a distance between the focus point and a transducer located farthest from the focus point from among the transducers included in the sub-array, a distance between the focus point and a transducer located in the middle of the transducers included in the sub-array, and an average of distances between the respective transducers included in the sub-array and the focus point, but is not limited thereto.

The ultrasound diagnosis apparatus 100 according to an embodiment may calculate a distance between the sub-array and the focus point by using the same criterion and calculate a time delay value based on the calculated result with respect to each of a plurality of sub-arrays.

Accordingly, the first digital beamformer 131 may generate a signal corresponding to at least one scan line included in a first ultrasound image 501 as illustrated in FIG. 7 by digital-beamforming signals respectively corresponding to sub-arrays. In this case, the first ultrasound image 501 may be a cross-sectional image perpendicular to a first direction (for example, the elevation direction), and the at least one scan line may be a scan line arranged in a second direction (for example, the lateral direction).

Accordingly, the image processor 140 may generate the first ultrasound image 501 as illustrated in FIG. 7 based on signals output from the first digital beamformer 131.

Meanwhile, the ultrasound diagnosis apparatus 100 according to an embodiment may perform multi-beam reception focusing that forms a plurality of multi-beams by transmitting an ultrasound beam to an object one time. For example, the 2D transducer array 110 may transmit an ultrasound signal to an object along one scan line, and receive an ultrasound signal reflected by the object. In this case, the ultrasound diagnosis apparatus 100 may generate a signal corresponding to a plurality of scan lines by using the reflected ultrasound signal.

The first digital beamformer 131 may perform multi-beam reception focusing in a direction (for example, the lateral direction) perpendicular to an analog beamforming direction (for example, the elevation direction) by applying different time delay values for each of the plurality of scan lines and performing digital beamforming when beamforming analog signals.

For example, in the case of forming four multi-beams by transmitting an ultrasound beam one time, a signal S1 corresponding to a first scan line SL1 may be generated by respectively applying time delay values a1, a2, ..., an to signals $E'_1, E'_2, \ldots, E'_N$ that are analog-beamformed in the elevation direction and digital-converted, and summing the same. Also, a signal S2 corresponding to a second scan line SL2 may be generated by applying time delay values b1, b2, ..., bn to the digital-converted signals $E'_1, E'_2, \ldots, E'_N$, respectively, and summing the same. Also, a signal S3 corresponding to a third scan line SL3 may be generated by applying time delay values c1, c2, ..., cn to the digital-converted signals $E'_1, E'_2, \ldots, E'_N$, respectively, and summing the same, and a signal S4 corresponding to a fourth scan line SL4 may be generated by applying time delay values d1, d2, ..., do to the digital-converted signals $E'_1, E'_2, \ldots, E'_N$, respectively, and summing the same. In this case, the first scan line to the fourth scan line SL1, SL2, SL3, and SL4 may be scan lines arranged in the lateral direction as illustrated in FIG. 7.

Also, the second digital beamformer 132 may perform digital beamforming by using a method similar to the method used by the first digital beamformer 131. Specifically, the second digital beamformer 132 may receive signals $L'_1, L'_2, \ldots, L'_M$ that are analog-beamformed in the lateral direction and digital-converted, and perform digital beamforming on the received signals. The second analog beamformer 132 may delay digital signals $L'_1, L'_2, \ldots, L'_M$ by a time delay calculated by taking into account a difference in a distance between each of (N+1)-th to (N+M)-th sub-arrays and a focus point, and then sum the delayed signals as one signal. Since a method of calculating a distance between the sub-array and the focus point has been described in detail in the above, description thereof is omitted.

The second digital beamformer 132 may generate a signal corresponding to at least one scan line included in a second ultrasound image 502 as illustrated in FIG. 7 by digital-beamforming signals corresponding to the sub-arrays, respectively. In this case, the second ultrasound image 502 may be a cross-sectional image perpendicular to the second direction (for example, the lateral direction), and the at least one scan line may be a scan line arranged in the first direction (for example, the elevation direction).

Accordingly, the image processor 140 may generate the second ultrasound image 502 as illustrated in FIG. 7 based on signals output from the second digital beamformer 132.

Also, the ultrasound diagnosis apparatus 100 according to an embodiment may perform multi-beam reception focusing in the elevation direction. For example, in the case of forming four multi-beams by transmitting an ultrasound beam one time, a signal S5 corresponding to a fifth scan line SL5 may be generated by respectively applying time delay values e1, e2, ..., en to signals $L'_1, L'_2, \ldots, L'_M$ that are analog-beamformed in the lateral direction and digital-converted, and summing the same. Also, a signal S6 corresponding to a sixth scan line SL6 may be generated by applying time delay values f1, f2, ..., fn to the digital-converted signals $L'_1, L'_2, \ldots, L'_M$, respectively, and summing the same. Also, a signal S7 corresponding to a seventh scan line SL7 may be generated by applying time delay values g1, g2, ..., gn to the digital-converted signals $L'_1, L'_2, \ldots, L'_M$, respectively, and summing the same. Also, a signal S8 corresponding to an eighth scan line SL8 may be generated by applying time delay values h1, h2, ..., hn to the digital-converted signals $L'_1, L'_2, \ldots, L'_M$, respectively, and summing the same. In this case, fifth to eighth scan lines may be scan lines arranged in the elevation direction as illustrated in FIG. 7.

The ultrasound diagnosis apparatus 100 according to an embodiment may raise a frame rate while maintaining resolution by performing multi-beam reception focusing. Also, the ultrasound diagnosis apparatus 100 may perform beamforming without an error by performing the multi-beam reception focusing in a direction perpendicular to a direction in which the analog beamforming has been performed.

FIGS. 8A to 8D are diagrams illustrating an example in which a first ultrasound image and a second ultrasound image are displayed on a display according to an embodiment.

Referring to FIG. 8A, the ultrasound diagnosis apparatus 100 may display a first ultrasound image 510 in a first region and display a second ultrasound image 520 in a second region.

The first ultrasound image 510 represents an image generated based on signals that are obtained by digital-beamforming signals that are analog-beamformed in the first direction, and the second ultrasound image 520 represents an image generated based on signals that are obtained by digital-beamforming signals that are analog-beamformed in the second direction. Accordingly, the first ultrasound image 510 and the second ultrasound image 520 are images corresponding to cross-sections perpendicular to each other. Also, the first ultrasound image 510 may be an ultrasound image corresponding to a cross-section perpendicular to the first direction, and the second ultrasound image 520 may be an ultrasound image corresponding to a cross-section perpendicular to the second direction.

Hereinafter, for convenience of description, description is made on the assumption that the first ultrasound image 510 is a cross-sectional image in the lateral direction, and the second ultrasound image 520 is a cross-sectional image in the elevation direction.

The ultrasound diagnosis apparatus 100 according to an embodiment may display 1' representing the first ultrasound image 510 is a cross-sectional image in the lateral direction in the first region, and display 'E' representing the second ultrasound image 520 is a cross-sectional image in the elevation direction in the second region.

Each of the first ultrasound image 510 and the second ultrasound image 520 according to an embodiment may be one of a B mode image, a color flow image, and an elastic image. Also, the first ultrasound image 510 and the second ultrasound image 520 may be images of different kinds. For example, as illustrated in FIG. 8, the first ultrasound image 510 may be a color Doppler image, and the second ultrasound image 520 may be a B mode image.

The ultrasound diagnosis apparatus 100 according to an embodiment may display icons 511 and 521 representing a B mode image, icons 512 and 522 representing a color flow image, and icons 513 and 523 representing an elastic image. In this case, the icons representing a B mode image, the icons representing a color flow image, and the icons representing an elastic image may be displayed in different colors. For example, the icons 511 and 521 representing a B mode image may be displayed in a first color, the icons 512 and 522 representing a color flow image may be displayed in a second color, and the icons 513 and 523 representing an elastic image may be displayed in a third color.

When receiving a user input that selects one of the displayed icons, the ultrasound diagnosis apparatus 100 may display an image of a kind corresponding to the selected icon. For example, when receiving a user input that selects the second icon 512 from among the first to third icons 511, 512, and 513 displayed in the first region, the ultrasound diagnosis apparatus 100 may display the first ultrasound image 510 by using a color flow image corresponding to the second icon 512. Also, when receiving a user input that selects the fourth icon 521 from among the fourth to sixth icons 521, 522, and 523 displayed in the second region, the ultrasound diagnosis apparatus 100 may display the second ultrasound image 520 by using a B mode image corresponding to the fourth icon 521. In this case, the selected second icon 512 and fourth icon 521 may be highlighted.

Referring to FIG. 8A again, the ultrasound diagnosis apparatus 100 may display the locations of a first cross-section 531 corresponding to the first ultrasound image 510 and a second cross-section 532 corresponding to the second ultrasound image 520. For example, the ultrasound diagnosis apparatus 100 may display the location of the first cross-section 531 corresponding to the first ultrasound image 510 and the location of the second cross-section 532 corresponding to the second ultrasound image 520 within a 3D volume 530, representing a scannable range by using the probe 101 according to an embodiment.

Also, the ultrasound diagnosis apparatus 100 may display a 2D region 540 corresponding to the 3D volume 530, and display a first movement bar 541 representing the location of the first cross-section 531 in a 1D line and a second movement bar 542 representing the location of the second cross-section 532 in a 1D line within the 2D region 540. Also, central reference lines may be displayed in a horizontal direction and a vertical direction on the 2D region 540 by using a dotted line. Accordingly, a degree in which the first cross-section 531 and the second cross-section 532 are separated from the center may be easily understood. Also, a vertical length H0 of the 2D region 540 and a coordinate value H1 of a vertical axis of the first movement bar 541 may be displayed in the first region in which the first ultrasound image 510 is displayed, and a horizontal length W0 of the 2D region 540 and a coordinate value W1 of a horizontal axis of the second movement bar 542 may be displayed in a region in which the second ultrasound image 520 is displayed.

Also, the color of the first movement bar 541 may be determined depending on a mode of the first ultrasound image 510, and the color of the second movement bar 542 may be determined depending on a mode of the second ultrasound image 520. For example, in the case where the first ultrasound image 510 is a color flow image, the first movement bar 541 may be displayed by using a second color, and in the case where the second ultrasound image 520 is a B mode image, the second movement bar 542 may be displayed by using a first color.

Also, the ultrasound diagnosis apparatus 100 may move the first movement bar 541 up and down by receiving a track ball input, a touch input, an up/down key input, etc. Also, the ultrasound diagnosis apparatus 100 may move the second movement bar 542 left and right by receiving a track ball input, a touch input, a left/right key input, etc. However, an input that moves the first movement bar 541 and the second movement bar 542 is not limited thereto.

When receiving a user input that moves the first movement bar 541 up and down, the ultrasound diagnosis apparatus 100 may move the first cross-section 531 in the elevation direction in response to the received user input. Also, when receiving a user input that moves the second movement bar 542 left and right, the ultrasound diagnosis apparatus 100 may move the second cross-section 532 in the lateral direction in response to the received user input.

Accordingly, the ultrasound diagnosis apparatus 100 may display the first ultrasound image corresponding to the moved first cross-section and the second ultrasound image corresponding to the moved second cross-section on the display 150.

Figure 8B:
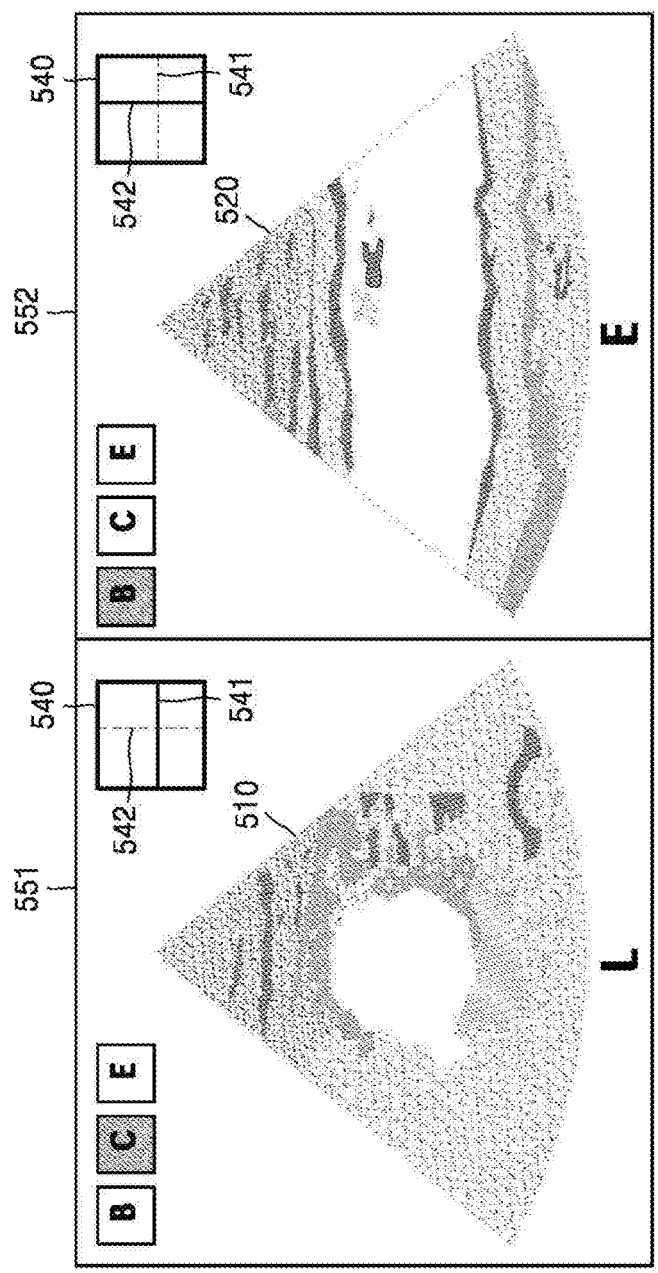

Referring to FIG. 8B, the ultrasound diagnosis apparatus 100 according to an embodiment may display the 2D region 540 including the first movement bar 541 and the second movement bar 542 in a first region 551 in which the first ultrasound image 510 is displayed, and in a second region 552 in which the second ultrasound image 520 is displayed. In this case, the first movement bar 541 displayed in the first region 551 may be displayed by using a solid line, and the second movement bar 542 may be displayed by using a dotted line. In this case, the location of the second movement bar 542 displayed in the first region 551 may be fixed, and only the location of the first movement bar 541 may be changed.

Also, the second movement bar 542 displayed in the second region 522 may be displayed by using a solid line, and the first movement bar 541 may be displayed by using a dotted line. In this case, the location of the first movement bar 541 displayed in the second region 522 may be fixed, and only the location of the second movement bar 542 may be changed.

Figure 8C:
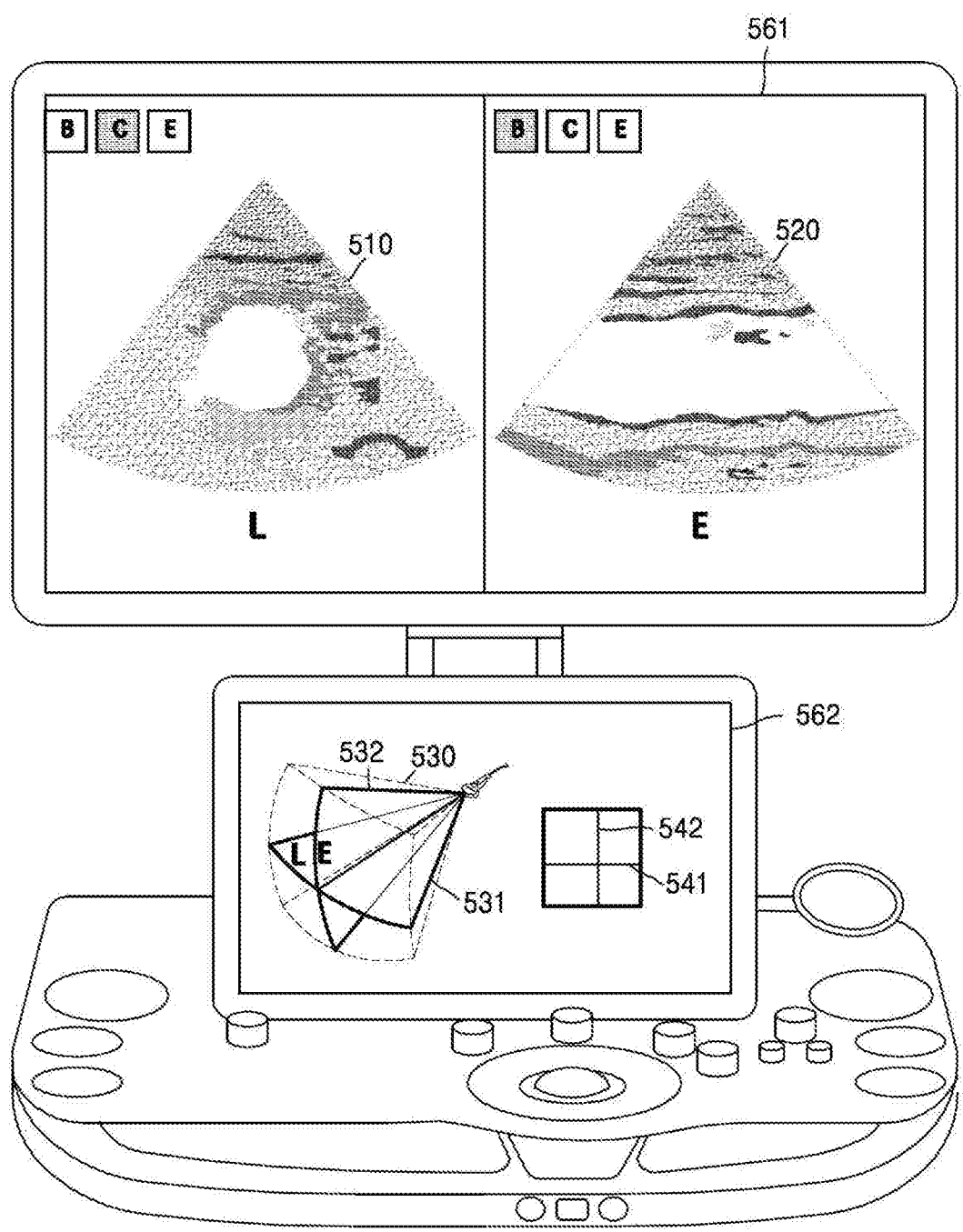

Referring to FIG. 8C, the ultrasound diagnosis apparatus 100 according to an embodiment may include a first display 561 and a second display 562. The first display 561 may display the first ultrasound image 510 and the second ultrasound image 520, and the second display 562 may display the locations of the first cross-section 531 corresponding to the first ultrasound image 510 and the second cross-section 532 corresponding to the second ultrasound image 520, and display the first movement bar 541 representing the location of the first cross-section 531 and the second movement bar 542 representing the location of the second cross-section 532.

Figure 8D:
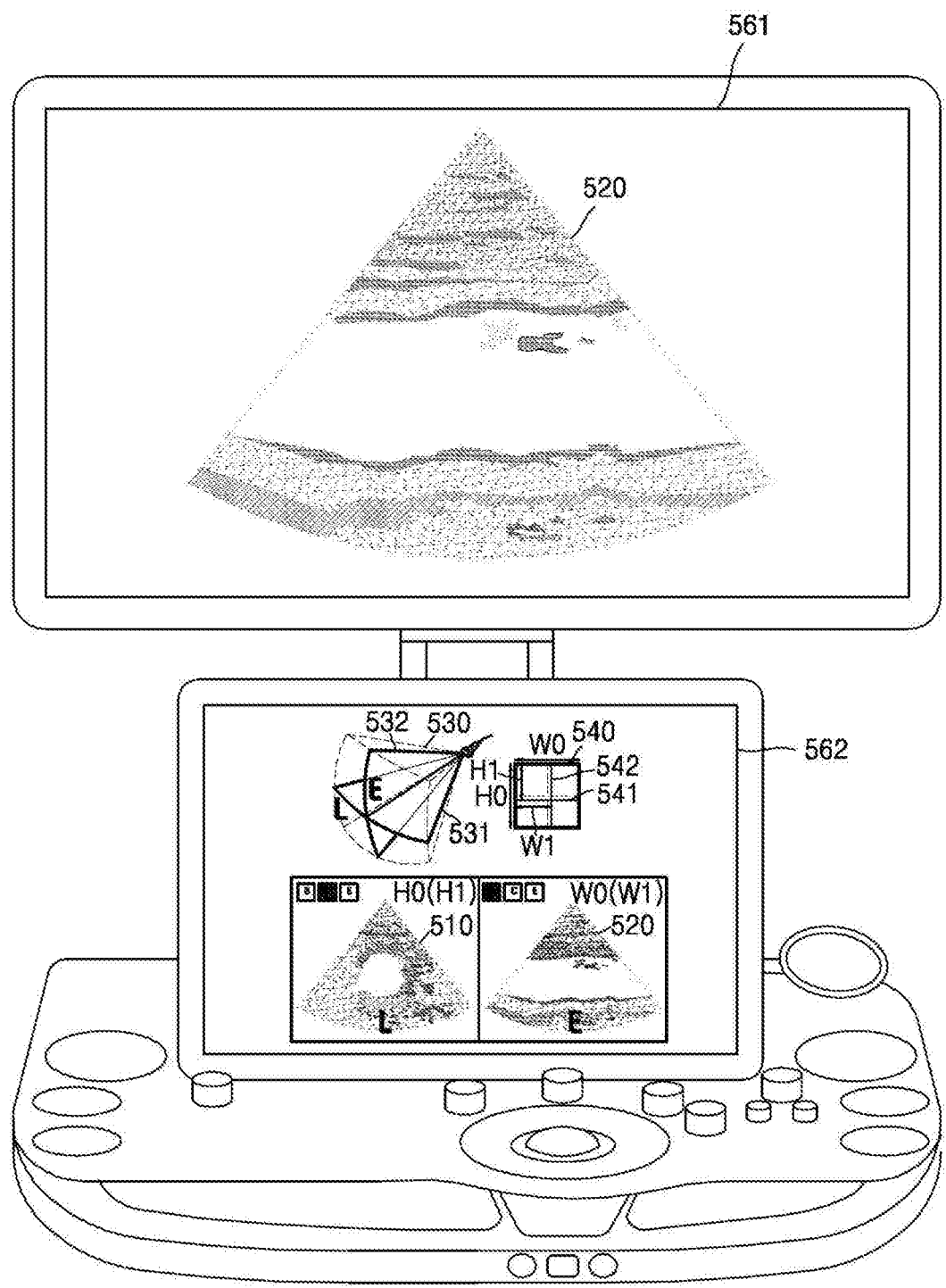

Referring to FIG. 8D, the ultrasound diagnosis apparatus 100 according to an embodiment may include the first display 561 and the second display 562. The second display 562 may display the first ultrasound image 510 and the second ultrasound image 520. Also, the second display 562 may display the locations of the first cross-section 531 corresponding to the first ultrasound image 510 and the second cross-section 532 corresponding to the second ultrasound image 520, and display the first movement bar 541 representing the location of the first cross-section 531 and the second movement bar 542 representing the location of the second cross-section 532.

In the case where one of the first ultrasound image 510 and the second ultrasound image 520 displayed in the second display 562 is selected, the first display 561 may display the selected image. For example, in the case where the second ultrasound image 520 is selected, the first display 561 may display the second ultrasound image 520 on an entire screen.

Figure 9:
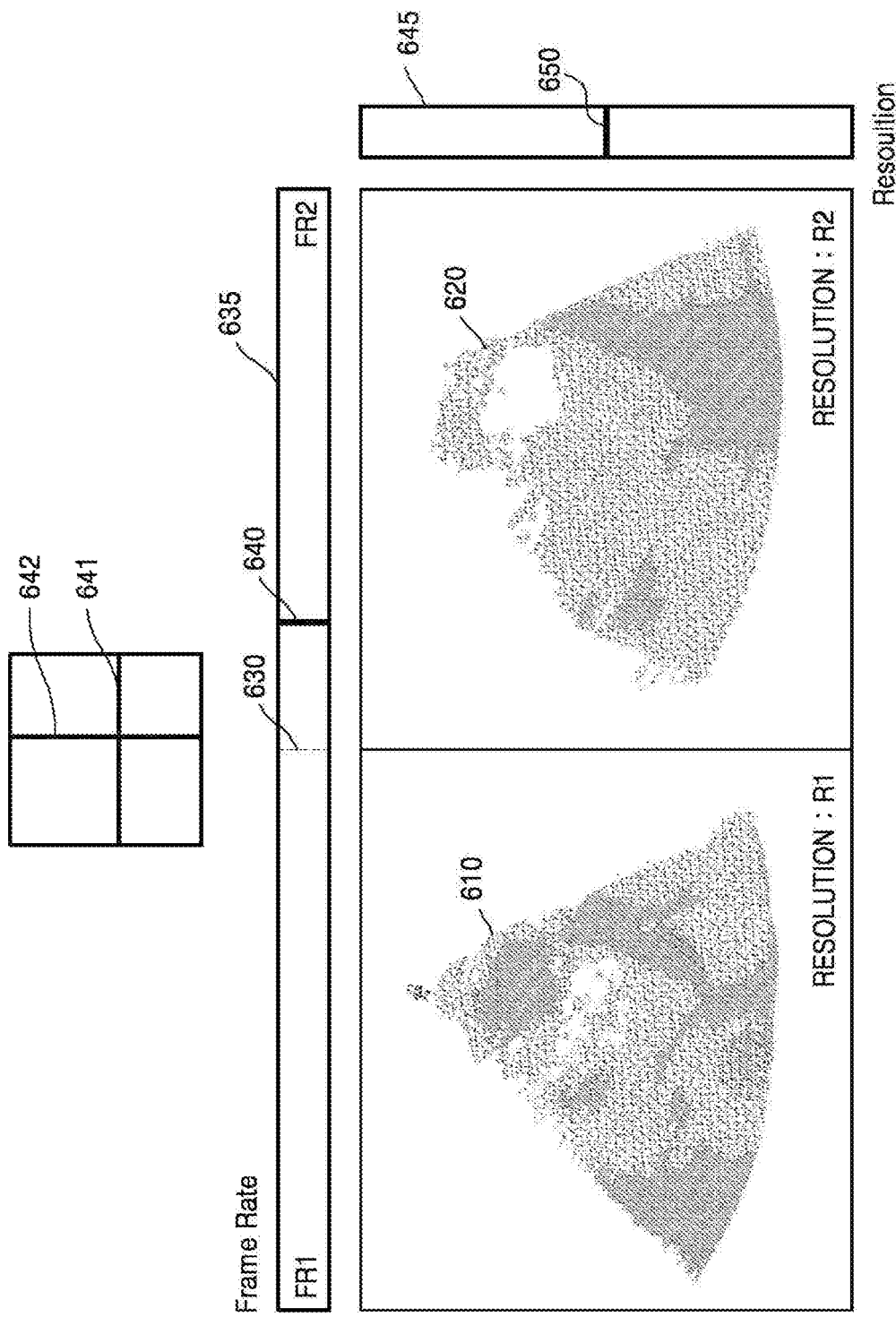
FIG. 9 is a diagram illustrating an example in which a user interface that adjusts a frame rate and resolution of ultrasound images is displayed on a display according to an embodiment.

FIG. 9 is a diagram illustrating an example in which a user interface that adjusts a frame rate and resolution of ultrasound images is displayed on a display according to an embodiment.

Referring to FIG. 9, the ultrasound diagnosis apparatus 100 may display a first ultrasound image 610 in a first region, and display a second ultrasound image 620 in a second region. Also, the ultrasound diagnosis apparatus 100 may display a first adjustment bar 640 that may adjust a frame rate of the first ultrasound image 610 and the second ultrasound image 620. In this case, the first adjustment bar 640 may move left and right within the first region 635. The first region 635 may be divided into a left region and a right region based on the first adjustment bar 640, and the left region and the right region may be displayed in different colors. Also, a frame rate of the first ultrasound image 610 and the second ultrasound image 620 may be determined depending on the location of the first adjustment bar 640 in the first region 635.

For example, in the case where the first adjustment bar 640 is located to the right from a middle line 630 (in this case, the left region is larger than the right region), the frame rate of the first ultrasound image 610 may be greater than the frame rate of the second ultrasound image 620. In contrast, in the case where the first adjustment bar 640 is located to the left from the middle line 630 (in this case, the left region is less than the right region), the frame rate of the second ultrasound image 620 may be greater than the frame rate of the first ultrasound image 610.

Also, the frame rate FR1 of the first ultrasound image 610 may be displayed in the left region, and the frame rate FR2 of the second ultrasound image 620 may be displayed in the right region. Also, colors displayed in the left region and the right region may be determined depending on the size of the frame rates of the first ultrasound image 610 and the second ultrasound image 620. For example, in the case where the frame rate of the first ultrasound image 610 is greater than the frame rate of the second ultrasound image 620, the left region may be displayed in a first color, and the right region may be displayed in a second color. In contrast, in the case where the frame rate of the first ultrasound image 610 is less than the frame rate of the second ultrasound image 620, the left region may be displayed in the second color, and the right region may be displayed in the first color. Also, in the case where the frame rate of the first ultrasound image 610 is the same as the frame rate of the second ultrasound image 620, the left region and the right region may be displayed in a third color, but is not limited thereto.

Also, when receiving an input that moves the first adjustment bar 640 to the right, the ultrasound diagnosis apparatus 100 may increase the frame rate of the first ultrasound image 610 and reduce the frame rate of the second ultrasound image 620 by increasing a number of multi-beams corresponding to the first ultrasound image 610 and reducing a number of multi-beams corresponding to the second ultrasound image 620. In contrast, when receiving an input that moves the first adjustment bar 640 to the left, the ultrasound diagnosis apparatus 100 may increase the frame rate of the second ultrasound image 620 and reduce the frame rate of the first ultrasound image 610 by increasing a number of multi-beams corresponding to the second ultrasound image 620 and reducing a number of multi-beams corresponding to the first ultrasound image 610.

However, the frame rate is not limited thereto, and the frame rate of the first ultrasound image 610 and the frame rate of the second ultrasound image 620 may be adjusted by using various methods. Also, contrary to the above-described method, when the first adjustment bar 640 is moved to the left, the frame rate of the first ultrasound image 610 may be increased and the frame rate of the second ultrasound image 620 may be reduced.

Referring to FIG. 9 again, the ultrasound diagnosis apparatus 100 may display the second adjustment bar 650 that may adjust resolution of the first ultrasound image 610 and the second ultrasound image 620. In this case, the second adjustment bar 650 may be moved up and down within the second region 645, and the resolution of the first ultrasound image 610 and the second ultrasound image 620 may be determined depending on the location of the second adjustment bar 650. For example, when the second adjustment bar 650 is located in the upper portion within the second region 645, resolution is high, and when the second adjustment bar 650 is located in the lower portion within the second region 645, resolution is low, but is not limited thereto.

Also, the resolution R1 of the first ultrasound image 610 may be displayed in a region in which the first ultrasound image 610 is displayed, and the resolution R2 of the second ultrasound image 620 may be displayed in a region in which the second ultrasound image 620 is displayed.

Also, the ultrasound diagnosis apparatus 100 may adjust the resolutions of the first ultrasound image 610 and the second ultrasound image 620, respectively, by using the second adjustment bar 650. For example, when receiving an input that selects the first ultrasound image 610 and moves the second adjustment bar 650 upward, the ultrasound diagnosis apparatus 100 may raise the resolution of the first ultrasound image 610. When receiving an input that selects the second ultrasound image 620 and moves the second adjustment bar 650 downward, the ultrasound diagnosis apparatus 100 may lower the resolution of the second ultrasound image 620.

For example, the ultrasound diagnosis apparatus 100 may raise resolution by increasing a number of scan lines included in an ultrasound image frame, and lower resolution by reducing a number of scan lines included in an ultrasound image frame. However, the method of adjusting resolution is not limited thereto, and the ultrasound diagnosis apparatus 100 may adjust resolution by using various methods.

Also, referring to FIG. 9, the ultrasound diagnosis apparatus 100 may display a first movement bar 641 and a second movement bar 642 respectively representing the locations of the first ultrasound image 610 and the second ultrasound image 620. Since the first movement bar 641 and the second movement bar 642 have been described in detail in FIG. 8A, descriptions thereof are omitted.

Figure 10A:
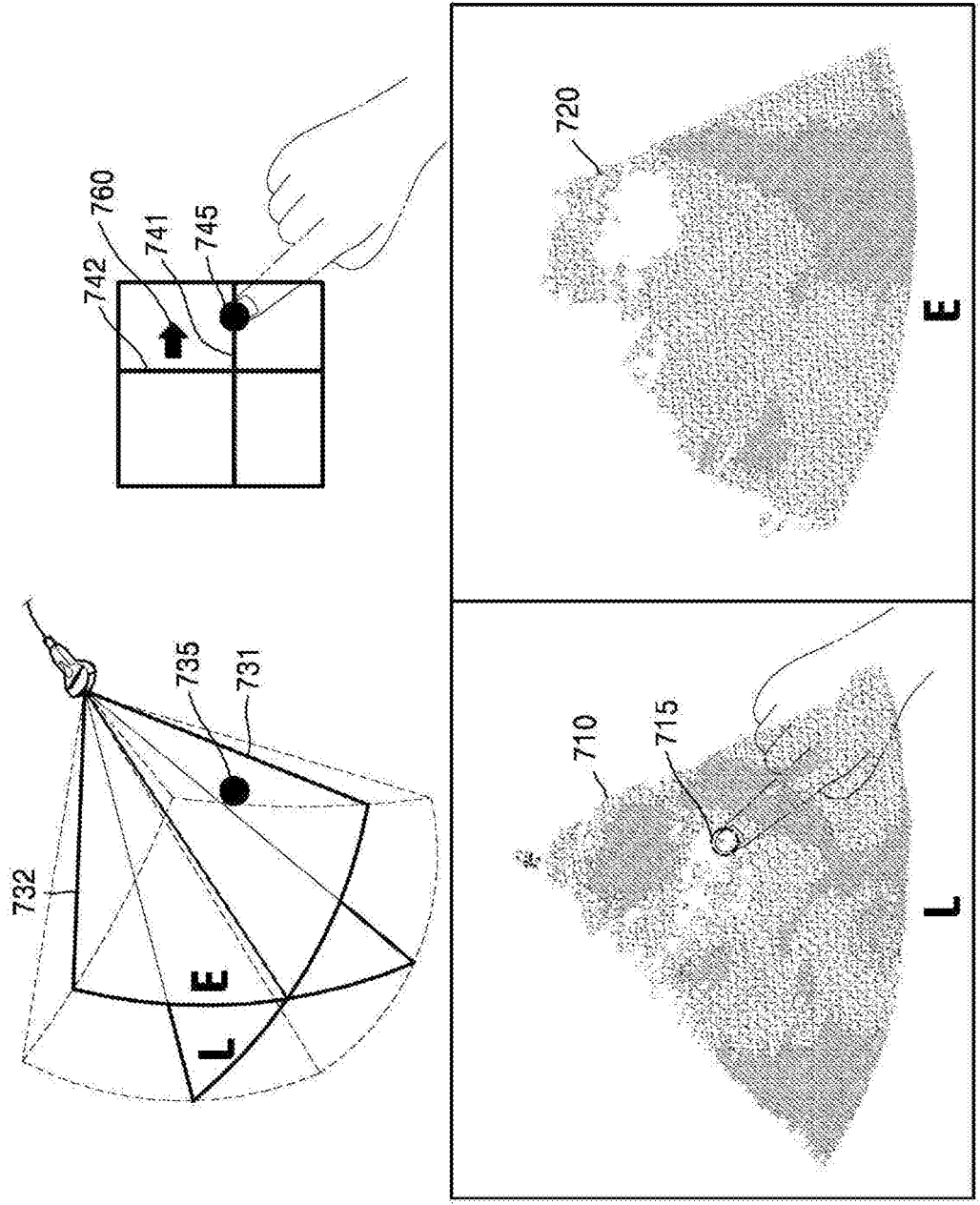
FIGS. 10A and 10B are diagrams illustrating an example in which an ultrasound diagnosis apparatus displays a second ultrasound image including a region of interest selected from a first ultrasound image according to an embodiment.
Figure 10B:
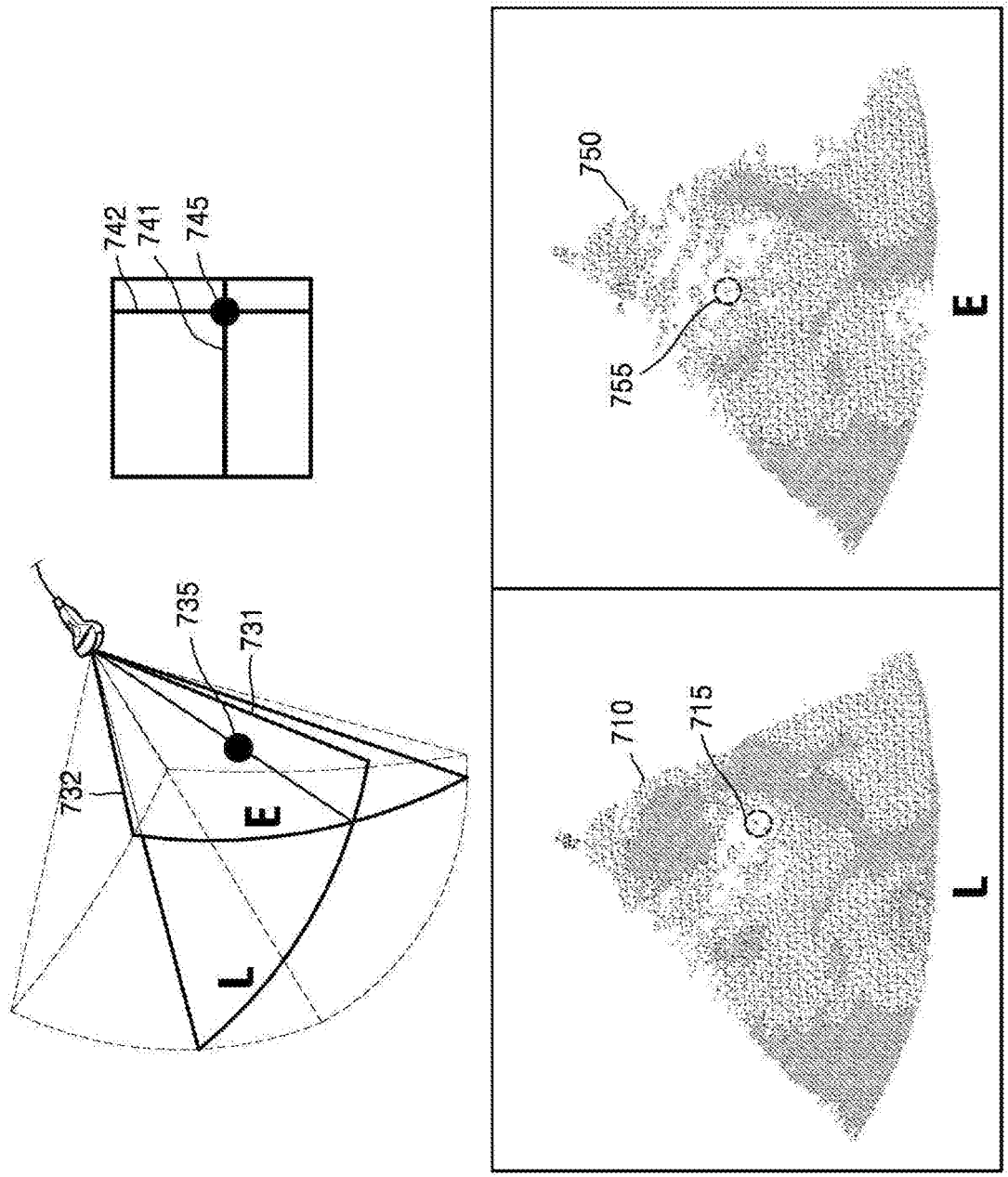

FIGS. 10A and 10B are diagrams illustrating an example in which an ultrasound diagnosis apparatus 100 displays a second ultrasound image including a region of interest selected from a first ultrasound image according to an embodiment.

Referring to FIGS. 10A and 10B, the ultrasound diagnosis apparatus 100 may display a first ultrasound image 710 in a first region and display a second ultrasound image 720 in a second region. Also, the ultrasound diagnosis apparatus 100 may display the locations of a first cross-section 731 corresponding to the first ultrasound image 710 and a second cross-section 732 corresponding to the second ultrasound image 720, and display a first movement bar 741 representing the location of the first cross-section 731 and a second movement bar 742 representing the location of the second cross-section 732. In this case, the first movement bar 741 may be moved up and down, and the second movement bar 742 may be moved left and right.

Meanwhile, as illustrated in FIG. 10A, the ultrasound diagnosis apparatus 100 may receive a user input that selects a region 715 of interest from the first ultrasound image 710, and display the region 715 of interest selected by the user input inside the first ultrasound image. In this case, the region 715 of interest selected by the user input may be a region not included in the second ultrasound image.

Also, the ultrasound diagnosis apparatus 100 may display a location 735 of the selected region of interest on the first cross-section 731 corresponding to the first ultrasound image 710, and display the location 735 on the first movement bar 741. Also, the ultrasound diagnosis apparatus 100 may simultaneously display a movement direction 760 of the second movement bar 742 that allows the region of interest to be located on the second movement bar 742. In this case, when receiving a user input that selects a location 745 of the region of interest displayed on the first movement bar 741, the ultrasound diagnosis apparatus 100 may move the second movement bar 741 to the relevant location 745 as illustrated in FIG. 10B. That is, the ultrasound diagnosis apparatus 100 may move the second movement bar 742 so that the location 745 of the region of interest may be located on the second movement bar 742. Alternatively, a user may move the second movement bar 742 to the region of interest by dragging the second movement bar 742 in the displayed movement direction 760, or performing a track ball input, and a left/right key input.

When the second movement bar 742 is moved so that the location 745 of the region of interest may be located on the second movement bar 742, the second cross-section 732 may be also moved to the location 735 of the region of interest. Accordingly, the ultrasound diagnosis apparatus 100 may generate a cross-sectional image in the elevation direction including a region 755 of interest as a second ultrasound image 750 and display the generated second ultrasound image 750 in the second region as illustrated in FIG. 10B.

Figure 11A:
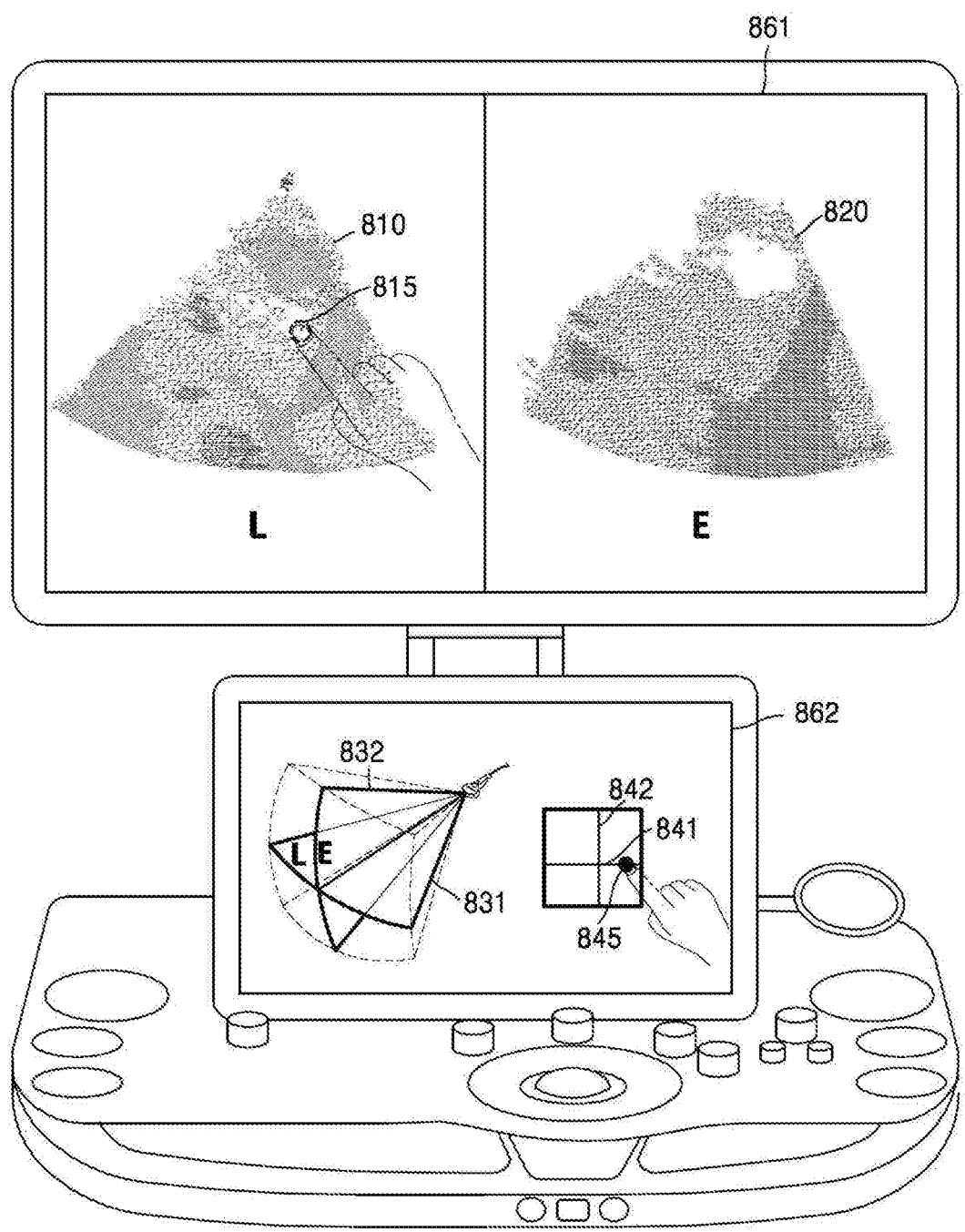
FIGS. 11A and 11B are views illustrating an example in which an ultrasound diagnosis apparatus displays a second ultrasound image including a region of interest selected from a first ultrasound image according to another embodiment.
Figure 11B:
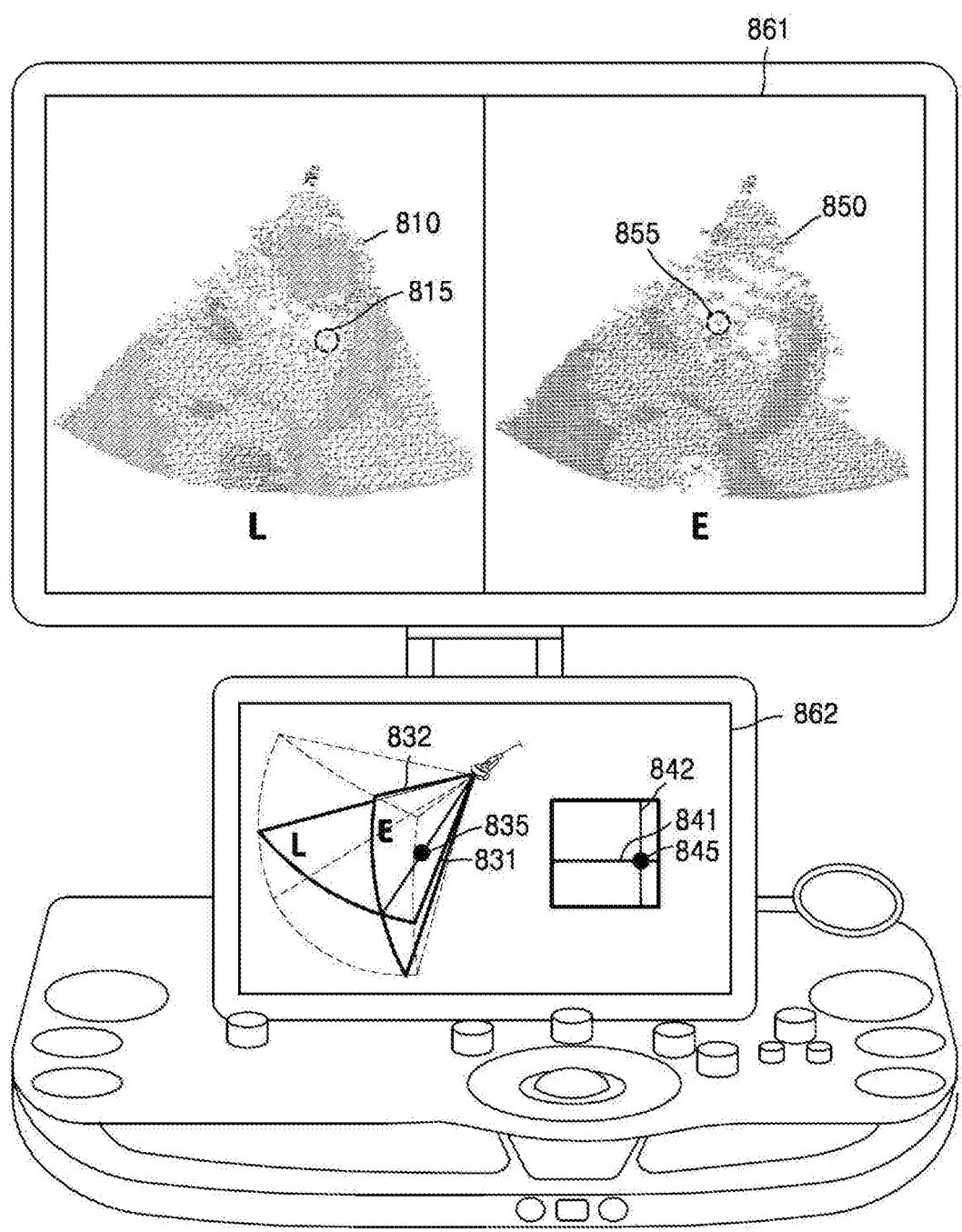

FIGS. 11A and 11B are views illustrating an example in which an ultrasound diagnosis apparatus 100 displays a second ultrasound image including a region of interest selected from a first ultrasound image according to another embodiment.

Referring to FIGS. 11A and 11B, the ultrasound diagnosis apparatus 100 may include a first display 861 and a second display 862. The first display 861 may display a first ultrasound image 810 and a second ultrasound image 820. The second display 862 may display the locations of a first cross-section 831 corresponding to the first ultrasound image 810 and a second cross-section 832 corresponding to the second ultrasound image 820, and display a first movement bar 841 representing the location of the first cross-section 831 and a second movement bar 842 representing the location of the second cross-section 832.

Meanwhile, as illustrated in FIG. 11A, the ultrasound diagnosis apparatus 100 may receive a user input that selects a region 815 of interest from the first ultrasound image 810. In this case, the region 815 of interest selected by the user input may be a region not included in the second ultrasound image 820.

Also, a location 835 of the selected region of interest may be displayed on the first cross-section 831 and the first movement bar 841. In this case, when receiving a user input that selects a location 845 of the region of interest displayed on the first movement bar 841, the ultrasound diagnosis apparatus 100 may move the second movement bar 842 to the relevant location 845 as illustrated in FIG. 11B. That is, the ultrasound diagnosis apparatus 100 may move the second movement bar 842 so that the location 845 of the region of interest may be located on the second movement bar 842. Alternatively, a user may move the second movement bar 842 to the region of interest by dragging the second movement bar 842, or performing a track ball input and a left/right key input.

When the second movement bar 842 is moved so that the location 845 of the region of interest may be located on the second movement bar 842, the second cross-section 832 may be also moved to the location 835 of the region of interest. Accordingly, the ultrasound diagnosis apparatus 100 may generate a cross-section image in the elevation direction including a region 855 of interest as a second ultrasound image 850 and display the generated second ultrasound image 850 on the first display 861 as illustrated in FIG. 11B.

FIG. 12 is a flowchart illustrating a method of operating an ultrasound diagnosis apparatus 100 according to an embodiment.

Referring to FIG. 12, the ultrasound diagnosis apparatus 100 according to an embodiment may include a 2D transducer array in which a plurality of transducers are arranged in two dimensions, may analog-beamform signals respectively corresponding to the plurality of transducers in a first direction, and analog-beamform the signals in a second direction perpendicular to the first direction (S1110).

For example, the ultrasound diagnosis apparatus 100 may perform analog-beamforming in the first direction by applying the same time delay value to transducers located on the same location in the second direction, and perform analog-beamforming in the second direction by applying the same time delay value to transducers located on the same location in the first direction. In this case, the first direction may be the elevation direction, and the second direction may be the lateral direction.

Also, the ultrasound diagnosis apparatus 100 according to an embodiment may digital-beamform signals that are analog-beamformed in the first direction, and digital-beamform signals that are analog-beamformed in the second direction (S1120).

For example, the ultrasound diagnosis apparatus 100 may generate signals corresponding to a plurality of scan lines arranged in the second direction by digital-beamforming signals that are analog-beamformed in the first direction. Also, the ultrasound diagnosis apparatus 100 may generate signals corresponding to a plurality of scan lines arranged in the first direction by digital-beamforming signals that are analog-beamformed in the second direction.

Also, the ultrasound diagnosis apparatus 100 according to an embodiment may generate a first ultrasound image by using a signal that is obtained by digital-beamforming signals that are analog-beamformed in the first direction, and generate a second ultrasound image by using signals that are obtained by digital-beamforming signals that are analog-beamformed in the second direction (S1130).

For example, the first ultrasound image and the second ultrasound image are images corresponding to cross-sections perpendicular to each other. Also, the first ultrasound image may be an ultrasound image corresponding to a cross-section perpendicular to the first direction, and the second ultrasound image may be an ultrasound image corresponding to a cross-section perpendicular to the second direction.

The ultrasound diagnosis apparatus 100 according to an embodiment may display the first ultrasound image and the second ultrasound image (S1140).

For example, each of the first ultrasound image and the second ultrasound image may be displayed as one of a B mode image, a color flow image, and an elastic image. Also, the ultrasound diagnosis apparatus 100 according to an embodiment may display the locations of a first cross-section corresponding to the first ultrasound image and a second cross-section corresponding to the second ultrasound image. Also, the ultrasound diagnosis apparatus 100 may display a first movement bar representing the location of the first cross-section and a second movement bar representing the location of the second cross-section. When the first movement bar or the second movement bar moves, the ultrasound diagnosis apparatus 100 may display the first ultrasound image corresponding to the moved first cross-section or the second ultrasound image corresponding to the moved second cross-section.

The ultrasound diagnosis apparatus 100 may display a first adjustment bar that may adjust the frame rate of the first ultrasound image and the second ultrasound image. Also, the ultrasound diagnosis apparatus 100 may display a second adjustment bar that may adjust the resolution of the first ultrasound image and the second ultrasound image.

According to an embodiment, a multi-beam may be implemented in the first direction and the second direction without an error. According to an embodiment, a multi-beam may be implemented in the first direction and the second direction, so that a frame rate of an ultrasound image may be increased. According to an embodiment, a number of cables connecting an analog beamformer with a digital beamformer may be reduced. According to an embodiment, an amount of operations by analog beamforming may be reduced.

Meanwhile, the ultrasound diagnosis apparatus and the method of operating the same according to embodiments can also be embodied as computer readable codes on a non-transitory computer readable recording medium. The non-transitory computer readable recording medium is any data storage device that can store data which can be thereafter read by a computer system. Examples of the non-transitory computer readable recording medium include read-only memory (ROM), random-access memory (RAM), CD-ROMs, magnetic tapes, floppy disks, optical data storage devices, and so on. The non-transitory computer readable recording medium can also be distributed over network coupled computer systems so that the computer readable code is stored and executed in a distributive manner.

While one or more embodiments have been described with reference to the figures, the inventive concept is not limited to the described specific embodiments and it will be understood by those of ordinary skill in the art that various changes in form and details may be made therein without departing from the spirit and scope as defined by the following claims. These modifications should not be individually understood from the technical spirit or prospect of the inventive concept.

What is claimed is:

1. An ultrasound diagnosis apparatus comprising:
a two-dimensional (2D) transducer array in which a plurality of transducers are arranged two dimensionally, the plurality of transducers transmitting ultrasound signals to a target object along one scan line, and receiving ultrasound echo signals reflected from the target object;
a first analog beamformer configured to perform analog beamforming in a first direction on the ultrasound echo signals to generate a plurality of first analog signals, based on first focus points;
a second analog beamformer configured to perform analog beamforming in a second direction perpendicular to the first direction on the ultrasound echo signals to generate a plurality of second analog signals, based on second focus points;
a digital beamformer configured to perform digital beamforming on the plurality of first analog signals to generate a plurality of first digital signals corresponding to a plurality of first scan lines based on the first analog signals beamformed in the first direction, for a first ultrasound image, and perform digital beamforming on the plurality of second analog signals to generate a plurality of second digital signals corresponding to a plurality of second scan lines based on the second analog signals beamformed in the second direction, for a second ultrasound image; and
an image processor configured to generate the first ultrasound image based on the plurality of first digital signals that are analog-beamformed in the first direction, and generate the second ultrasound image based on the plurality of second digital signals that are analog-beamformed in the second direction; and
a display configured to display the first ultrasound image and the second ultrasound image.

2. The apparatus of claim 1, wherein the first analog beamformer performs the analog beamforming in the first direction by applying a same time delay value to transducers located at same locations in the second direction; and
wherein the second analog beamformer performs the analog beamforming in the second direction by applying a same time delay value to transducers located at same locations in the first direction.

3. The apparatus of claim 1, wherein the 2D transducer array comprises an M×N 2D transducer array in which M 1D transducers are arranged in an elevation direction, and N 1D transducers are arranged in a lateral direction,
wherein the first analog beamformer performs the analog beamforming in the lateral direction on each of the M 1D transducers arranged in the elevation direction, and
wherein the second analog beamformer performs the analog beamforming in the elevation direction on each of the N 1D transducers arranged in the lateral direction.

4. The apparatus of claim 3, wherein a number of channels input to the digital beamformer is M+N.

5. The apparatus of claim 1, wherein the first ultrasound image comprises an image corresponding to a first cross-section of the target object, the second ultrasound image comprises an image corresponding to a second cross-section of the target object, and the first cross-section is perpendicular to the second cross-section.

6. The apparatus of claim 5, wherein the display further comprises a 2D region, and
wherein the 2D region displays a first movement bar representing a location of the first cross-section in a 1D line.

7. The apparatus of claim 6, wherein the first movement bar moves up and down by receiving a track ball input, a touch input, and an up/down key input.

8. The apparatus of claim 6, wherein a vertical length of the 2D region and a coordinate value of a vertical axis of the first movement bar is displayed in a first region in which the first ultrasound image is displayed.

9. The apparatus of claim 5, wherein the display further comprises a 2D region, and
wherein the 2D region displays a second movement bar representing a location of the second cross-section in a 1D line.

10. The apparatus of claim 9, wherein the second movement bar moves left and right by receiving a track ball input, a touch input, and a left/right key input.

11. The apparatus of claim 9, wherein a horizontal length of the 2D region and a coordinate value of a horizontal axis of the second movement bar is displayed in a second region in which the second ultrasound image is displayed.

12. The apparatus of claim 1, wherein each of the first ultrasound image and the second ultrasound image comprises one of a brightness (B) mode image, a color flow image, and an elastic image.

13. The apparatus of claim 1, wherein the display is further configured to display an adjustment bar that adjusts resolutions of the first ultrasound image and the second ultrasound image.

14. The apparatus of claim 1, wherein the display further comprises a 2D region, and
wherein the 2D region comprises:
a first central reference line displayed in the first direction; and
a second central reference line displayed in the second direction perpendicular to the first direction.

15. The apparatus of claim 1, wherein the first direction is an elevation direction, and the second direction is a lateral direction.

16. A method of operating an ultrasound diagnosis apparatus comprising a two-dimensional (2D) transducer array in which a plurality of transducers are arranged two dimensionally, the method comprising:
transmitting ultrasound signals to a target object along one scan line, and receiving ultrasound echo signals reflected from the target object;
performing analog beamforming in a first direction on the ultrasound echo signals to generate a plurality of first analog signals, based on first focus points, and performing analog beamforming in a second direction perpendicular to the first direction on the ultrasound echo signals to generate a plurality of second analog signals, based on second focus points;
performing digital beamforming on the plurality of first analog signals to generate a plurality of first digital signals corresponding to a plurality of first scan lines based on the first analog signals beamformed in first direction, for a first ultrasound image, and performing digital beamforming on the plurality of second analog signals to generate a plurality of second digital signals corresponding to a plurality of second scan lines based on the second analog signals beamformed in the second direction, for a second ultrasound image;
generating the first ultrasound image based on the plurality of first digital signals that are analog-beamformed in the first direction, and generating the second ultrasound image based on the plurality of second digital signals that are analog-beamformed in the second direction; and
displaying the first ultrasound image and the second ultrasound image.

17. The method of claim 16, wherein the performing of the analog beamforming in the first direction, and the performing of the analog beamforming in the second direction perpendicular to the first direction comprises:
performing the analog beamforming in the first direction by applying a same time delay value to transducers located at a same location in the second direction; and
performing the analog beamforming in the second direction by applying a same time delay value to transducers located at a same location in the first direction.

18. The method of claim 16, wherein the 2D transducer array comprises an M×N 2D transducer array in which M 1D transducers are arranged in an elevation direction, and N 1D transducers are arranged in a lateral direction,
the performing of the analog beamforming in the first direction, and the performing of the analog beamforming in the second direction perpendicular to the first direction comprise:
performing the analog beamforming in the lateral direction on each of the M 1D transducers arranged in the elevation direction, and performing the analog beamforming in the elevation direction on each of the N 1D transducers arranged in the lateral direction.

19. The method of claim 16, wherein the first ultrasound image comprises an image corresponding to a first cross-section of the target object, the second ultrasound image comprises an image corresponding to a second cross-section of the target object, and the first cross-section is perpendicular to the second cross-section.

20. The method of claim 19, further comprising displaying a 2D region,
wherein the 2D region displays a first movement bar representing a location of the first cross-section in a 1D line.

21. The method of claim 20, wherein the first movement bar moves up and down by receiving a track ball input, a touch input, and an up/down key input.

22. The method of claim 20, wherein a vertical length of the 2D region and a coordinate value of a vertical axis of the first movement bar is displayed in a first region in which the first ultrasound image is displayed.

23. The method of claim 19, further comprising displaying a 2D region,
wherein the 2D region displays a second movement bar representing a location of the second cross-section in a 1D line.

24. The method of claim 23, wherein the second movement bar moves left and right by receiving a track ball input, a touch input, and a left/right key input.

25. The method of claim 23, wherein a horizontal length of the 2D region and a coordinate value of a horizontal axis of the second movement bar is displayed in a second region in which the second ultrasound image is displayed.

26. The method of claim 16, wherein each of the first ultrasound image and the second ultrasound image comprises one of a B mode image, a color flow image, and an elastic image.

27. The method of claim 16, further comprising:
displaying an adjustment bar that adjusts resolutions of the first ultrasound image and the second ultrasound image.

28. The method of claim 16, further comprising displaying a 2D region,
wherein the 2D region comprises:
a first central reference line displayed in the first direction; and a second central reference line displayed in the second direction perpendicular to the first direction.

29. The method of claim 16, wherein the first direction is an elevation direction, and the second direction is a lateral direction.

30. An ultrasound diagnosis apparatus comprising:
  a two-dimensional (2D) transducer array in which a plurality of transducers are arranged two dimensionally, the plurality of transducers transmitting ultrasound signals to a target object along one scan line, and receiving ultrasound echo signals reflected from the target object;
  a first analog beamformer configured to perform analog beamforming in a first direction on the ultrasound echo signals to generate a plurality of first analog signals, based on first focus points;
  a second analog beamformer configured to perform analog beamforming in a second direction perpendicular to the first direction on the ultrasound echo signals to generate a plurality of second analog signals, based on second focus points;
  a digital beamformer configured to perform digital beamforming on the plurality of first analog signals to generate a plurality of first digital signals corresponding to a plurality of first scan lines based on the first analog signals beamformed in the first direction, for a first ultrasound image, and perform digital beamforming on the plurality of second analog signals to generate a plurality of second digital signals corresponding to a plurality of second scan lines based on the second analog signals beamformed in the second direction, for a second ultrasound image; and
  an image processor configured to generate the first ultrasound image based on the plurality of first digital signals that are analog-beamformed in the first direction, and generate the second ultrasound image based on the plurality of second digital signals that are analog-beamformed in the second direction; and
  a display configured to display the first ultrasound image and the second ultrasound image,
  wherein the first ultrasound image is fixed, and a plane of the second ultrasound image is movable along the first ultrasound image.

* * * * *